(12) United States Patent
Kathirgamanathan et al.

(10) Patent No.: US 8,642,188 B2
(45) Date of Patent: Feb. 4, 2014

(54) PHENANTHROLINE COMPOUNDS AND ELECTROLUMINESCENT DEVICES USING THE SAME

(75) Inventors: Poopathy Kathirgamanathan, North Harrow (GB); Sivagnanasundram Surendrakumar, Middlesex (GB)

(73) Assignee: Merck Patent GmbH, Darmstadt (DE)

( * ) Notice: Subject to any disclaimer, the term of this patent is extended or adjusted under 35 U.S.C. 154(b) by 743 days.

(21) Appl. No.: 12/520,349

(22) PCT Filed: Dec. 19, 2007

(86) PCT No.: PCT/GB2007/050768
§ 371 (c)(1),
(2), (4) Date: Nov. 4, 2009

(87) PCT Pub. No.: WO2008/078115
PCT Pub. Date: Jul. 3, 2008

(65) Prior Publication Data
US 2010/0060152 A1    Mar. 11, 2010

(30) Foreign Application Priority Data

Dec. 22, 2006  (GB) .................................. 0625540.0

(51) Int. Cl.
H01L 51/54  (2006.01)

(52) U.S. Cl.
USPC ........... 428/690; 428/917; 313/504; 313/505; 313/506; 257/40; 257/E51.05; 257/E51.026; 257/E51.032; 584/418; 584/440; 546/79; 546/81; 546/101; 564/26; 564/426; 564/434

(58) Field of Classification Search
USPC ................ 428/690, 917; 313/504, 505, 506; 257/40, E51.05, E51.026, E51.032; 548/440, 304.4, 418; 546/79, 81, 101; 564/26, 426, 434
See application file for complete search history.

(56) References Cited

U.S. PATENT DOCUMENTS

| | | | |
|---|---|---|---|
| 4,356,429 A | 10/1982 | Tang | |
| 4,720,432 A | 1/1988 | VanSlyke et al. | |
| 4,769,292 A * | 9/1988 | Tang et al. ..................... | 428/690 |
| 5,141,671 A | 8/1992 | Bryan et al. | |
| 6,208,075 B1 | 3/2001 | Hung et al. | |
| 8,129,037 B2 * | 3/2012 | Stossel et al. ................. | 428/690 |
| 2003/0057827 A1 * | 3/2003 | Kido et al. ..................... | 313/504 |
| 2003/0186079 A1 * | 10/2003 | Towns et al. .................. | 428/690 |
| 2006/0003089 A1 | 1/2006 | Kathirgamanathan | |
| 2006/0072053 A1 * | 4/2006 | Kathirgamanathan et al. . | 349/69 |
| 2006/0079004 A1 | 4/2006 | Werner et al. | |
| 2007/0065180 A1 * | 3/2007 | Yatsunami .................... | 399/220 |
| 2007/0259208 A1 * | 11/2007 | Kathirgamanathan et al. ............. | 428/690 |
| 2009/0026919 A1 | 1/2009 | Stossel et al. | |

FOREIGN PATENT DOCUMENTS

| | | | | |
|---|---|---|---|---|
| EP | 0891121 A1 | 1/1999 | | |
| EP | 1029909 A1 | 8/2000 | | |
| EP | 1035213 A1 | 9/2000 | | |
| EP | 1645610 | * 10/2004 | ............. | C09K 11/06 |
| EP | 1645610 A1 | 4/2006 | | |
| JP | 07-053951 | * 2/1995 | ............. | C09K 11/06 |
| JP | 2001-267080 | * 9/2001 | ............. | C09K 11/06 |
| WO | WO-00/32717 A1 | 6/2000 | | |
| WO | WO-03/006573 A1 | 1/2003 | | |
| WO | WO-03/007663 A1 | 1/2003 | | |
| WO | WO-2004/005288 A2 | 1/2004 | | |
| WO | WO-2004/050793 A1 | 6/2004 | | |
| WO | WO-2004/058783 A1 | 7/2004 | | |
| WO | WO-2004/058913 A1 | 7/2004 | | |
| WO | WO-2004/084325 A1 | 9/2004 | | |
| WO | WO-2005/080526 A2 | 9/2005 | | |
| WO | WO-2006/004138 A1 | 1/2006 | | |
| WO | WO-2006/016193 A1 | 2/2006 | | |
| WO | WO 2006/024878 | * 3/2006 | ............. | C07F 15/00 |
| WO | WO-2006/024878 A1 | 3/2006 | | |
| WO | WO-2006/040593 A1 | 4/2006 | | |
| WO | WO-2006/087521 A1 | 8/2006 | | |
| WO | WO-2006/090098 A1 | 8/2006 | | |
| WO | WO-2007/052083 A2 | 5/2007 | | |
| WO | WO-2008/078114 A1 | 7/2008 | | |

OTHER PUBLICATIONS

Tanaka et al., Ortho-Fused Heterocyclic Derivatives as Efficient Eleectroluminescent Materials, 2002, Bulletin of the Chemical Society of Japan, vol. 75, pp. 551-557.*
Cammarata et al., Langmuir-Schaefer Films of Distyrylphenanthrolines and Rhenium Tricarbonyl Chloride Complexes: Headgroup Influence on Anisotropy, 1996, Langmuir, vol. 12, pp. 4882-4888.*
Yang et al., Novel Photochemical Behavior of Olefin with a Pyrrole Ring and a Phenthroline Ring Controlled by Hydrogen Bonding, 1998, Tetrahedron Letters, vol. 39, pp. 2617-2620.*
Achremowicz, L., "Investigations on Reactivity of Phenanthrolines Part IX, Extension of 1,7- and 1,8-Phenanthroline Systems by Azaaromatic Rings", Polish Journal of Chemistry, (1980), vol. 54, pp. 2365-2371.
Aloui, F., et. al., "Synthesis and X-Ray Analysis of a New [6] Helicene", Synthetic Communications, (2006), vol. 36, pp. 1557-1567.

(Continued)

Primary Examiner — Gregory Clark
(74) Attorney, Agent, or Firm — Novak Druce Connolly Bove + Quigg LLP

(57) ABSTRACT

In OLEDs, improved efficiency is obtained by using compounds of formula $[Ar](CH=CH-R_1)_n$ wherein n is an integer from 1 to 4; [Ar] is a polycyclic aromatic or heteroaromatic scaffold optionally substituted with one or more alkyl or alkoxy groups; and $R_1$ is a 5-membered heteroaryl group optionally substituted with methyl, methoxy, aryl or heteroaryl, or is phenyl or naphthyl optionally substituted with methyl, methoxy, trifluoromethyl or cyano or is biphenyl or substituted biphenyl. The compounds are believed to be novel and can be made by condensing a compound of formula wherein [Ar] and n are as defined above with a compound of formula $[Ar](CH3)_nR_1CHO$ in the presence of an acid catalyst e.g. an anhydride of an organic acid.

34 Claims, 6 Drawing Sheets

(56) References Cited

OTHER PUBLICATIONS

Balasubramanian, K., et. al., "Langmuir-Schaefer Films of Distyrylphenanthrolines and Rhenium Tricarbonyl Chloride Complexes: Headgroup Influence on Anisotrophy", Langmuir, (1996), vol. 12, pp. 4882-4888.

Boden, B., et. al., "Tetraalkoxyphenanthrene: A New Precursor for Luminescent Conjugated Polymers", Organic Letters, (2006), vol. 8, No. 9, pp. 1855-1858.

Case, F., et. al., "Substituted 1,10-Phenanthrolines, XL. Aza Derivatives", JACS, (1959), vol. 81, pp. 6297-6301.

Sykes, W., et. al., "Monomethiodides of Some 3-Substituted 4:7-Phenanthrolines", Journal of the Chemical Society, (1956), pp. 3087-3092.

Yang, Y., et. al., "Novel Phtochemical Behavior of Olefin with a Pyrrole Ring and Phenanthroline Ring Controlled by Hydrogen Bonding", Tetrahedron Letters, (1998), vol. 39, pp. 2617-2620.

\* cited by examiner

Absorption and Fluorescent Spectra of Thinfilm of Compound A

Absorption and Fluorescent Spectra of Compound A in Solution (THF)

Fluorescent Red Device
Compound A as an ETL: Comparison with $Zrq_4$
ITO/CuPc (20)/α-NPB (50)/$Alq_3$:DCJTi (60:0.6)/ETL (20)/LiF (0.3)/Al Fluorescent Red Device
Compound A as an ETL: Comparison with $Zrq_4$
ITO/CuPc (20)/α-NPB (50)/$Alq_3$:DCJTi (60:0.6)/ETL (20)/LiF (0.3)/Al

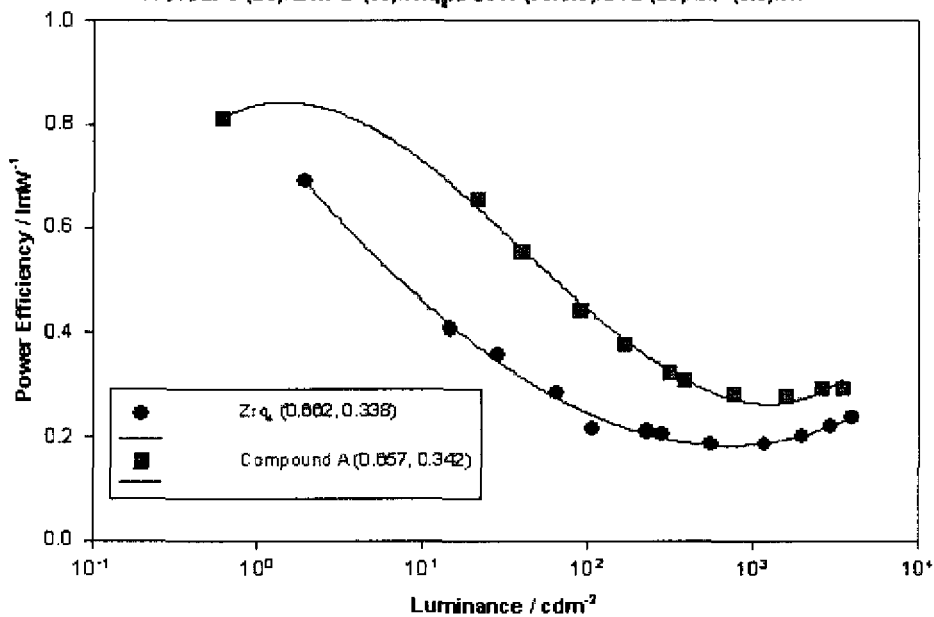
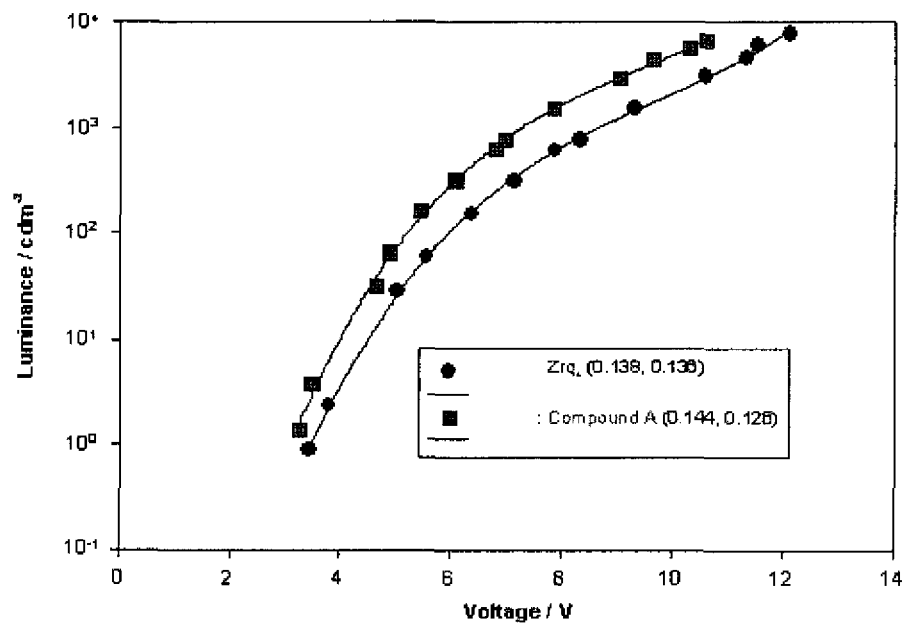

Fluorescent Blue Device
Compound A as an ETL: Comparison with Zrq$_4$
ITO/ZnTpTP (20)/α-NPB (50)/Compound H:Perylene (25:0.1)/ETL (20)/LiF (0.3)/Al Fluorescent Blue Device
Compound A as an ETL: Comparison with Zrq$_4$
ITO/ZnTpTP (20)/α-NPB (50)/Compound H:Perylene (25:0.1)/ETL (20)/LiF (0.3)/Al

PHENANTHROLINE COMPOUNDS AND ELECTROLUMINESCENT DEVICES USING THE SAME

FIELD OF THE INVENTION

This invention relates to a novel compound and to its use in inter alia optical light emitting devices e.g. as a host in an electroluminescent layer or in an electron transport layer.

BACKGROUND TO THE INVENTION

Kulkarni et al., *Chem. Mater.* 2004, 16, 4556-4573 (the contents of which are incorporated herein by reference) have reviewed the literature concerning electron transport materials (ETMs) used to enhance the performance of organic light-emitting diodes (OLEDs). In addition to a large number of organic materials, they discuss metal chelates including aluminium quinolate, which they explain remains the most widely studied metal chelate owing to its superior properties such as high EA EA (~−3.0 eV; measured by the present applicants as −2.9 eV) and IP (~−5.95 eV; measured by the present applicants as about −5.7 eV), good thermal stability (Tg ~172° C.) and ready deposition of pinhole-free thin films by vacuum evaporation. Aluminium quinolate remains a preferred material both for use as a host to be doped with various fluorescent materials to provide an electroluminescent layer and for use as an electron transport layer.

SUMMARY OF THE INVENTION

A problem with which invention is concerned is to provide OLEDs of improved performance. A further problem with which the invention is concerned is to provide further materials for use in the electroluminescent and/or or electron transport layer of an OLED.

In one aspect the invention provides compounds of formula

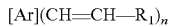

wherein
n is an integer from 1 to 4;
[Ar] is a polycyclic aromatic or heteroaromatic scaffold optionally substituted with one or more alkyl or alkoxy groups; and
$R_1$ is a 5-membered heteroaryl group optionally substituted with methyl, methoxy, aryl or heteroaryl, or is phenyl or naphthyl optionally substituted with methyl, methoxy, trifluoromethyl or cyano or is biphenyl or substituted biphenyl.

In embodiments Ar has three or more fused rings, in embodiments 3-5 fused rings, e.g. anthracene, phenanthrene, chrysene, perylene pyrene, benzopyrene, tetracene, pentacene and similar heterocyclics e.g benzoquinoline, acridene, benzonaphthyridine and phenanthroline. Embodiments of the invention are based on tricylcic heteroaromatics with two or more nitrogen atoms in the ring system including in particular various isomers of phenanthroline including 1,7-phenanthroline, 1,10-phenanthroline, and 4,7-phenanthroline, 1,10-phenanthroline being the most common. The phenanthroline nucleus may be substituted with one or more substituents e.g. alkyl groups or alkoxy groups e.g. methyl as in 4-methyl-1,10-phenanthroline, 5-methyl-1,10-phenanthroline, 4,7-dimethyl-1,10-phenanthroline, 2,9-dimethyl-1,10-phenanthroline, 2,5,9-trimethyl-1,10-phenanthroline and 3,4,7,8-tetramethyl-1,10-phenanthroline or methoxy as in 4,7-dimethoxy-1,10-phenanthroline. Methyl substituted phenanthrolines and other nitrogen containing heteroaromatics may be reacted with aldehydes to convert one or more of the methyl groups present into —CH=CH—$R_1$ groups.

In a further aspect, the invention provides the compound 2,9-Bis(2-thiophen-2-yl-vinyl)-[1,10]phenanthroline, i.e. the compound of formula:

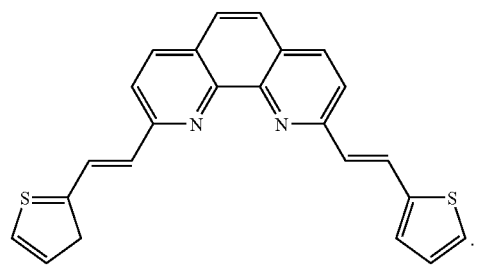

The invention also provides a process for making a compound of the formula set out in above, which comprises by condensing a compound of formula

wherein [Ar] and n are as defined in claim 1 with a compound of formula $R_1$CHO wherein R1 is as defined in claim 1 in the presence of an acid catalyst. The invention also provides a composition (which may be formed in situ and may for example be a layer in an OLED or other electro-optical device) comprising a compound of formula

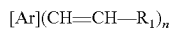

wherein
n is an integer from 1 to 4;
[Ar] is a polycyclic aromatic or heteroaromatic scaffold optionally substituted with one or more alkyl or alkoxy groups; and
$R_1$ is a 5-membered heteroaryl group optionally substituted with methyl, methoxy, aryl or heteroaryl, or is phenyl or naphthyl optionally substituted with methyl, methoxy, trifluoromethyl or cyano or is biphenyl or is substituted biphenyl and another organic semiconductor or metal. In some embodiments the compound may be doped with a metal, in other embodiments it may be mixed with another electron transport material e.g. a metal quinolate or substituted quinolate and in further embodiments it may be doped with a fluorescent dopant, doped with a phosphorescent dopant or doped with a rare earth chelate.

In a further aspect, the invention provides an electro-optical or opto-electronic device having a layer comprising a compound as defined above e.g. 2,9-Bis(2-thiophen-2-yl-vinyl)-[1,10] phenanthroline. Such devices include OLEDs and also e.g. organic phototransistors, organic photovoltaic cells, organic photodetectors, electronic storage devices based on bistable organic molecules and photoconductive imaging members for creating electrostatic latent images.

In a yet further aspect the invention provides an optical light emitting diode device having a first electrode, a layer comprising a compound as defined above e.g. 2,9-Bis(2-thiophen-2-yl-vinyl)-[1,10] phenanthroline and a second electrode.

In an embodiment there is provided an optical light emitting diode device having an electroluminescent layer and an electron transport layer, wherein the electron transport layer comprises a compound as defined above e.g. 2,9-Bis(2-thiophen-2-yl-vinyl)-[1,10] phenanthroline. It has been found that 2,9-Bis(2-thiophen-2-yl-vinyl)-[1,10] phenanthroline, when used in an electron transport layer of an OLED increases efficiency even above that which is obtained when zirconium quinolate is used, zirconium quinolate being a material of exceptionally high efficiency for that purpose, and this behaviour is shared by other compounds as defined above. Embodiments of OLEDS incorporating the above compounds in their electron transport layer should exhibit reduced turn-on voltage and increased device lifetime. The compounds as defined above e.g. 2,9-Bis(2-thiophen-2-yl-vinyl)-[1,10] phenanthroline may also be used as host materials in the electroluminescent layer, being dopable with one or more fluorescent or phosphorescent dopants as described below.

BRIEF DESCRIPTION OF THE DRAWINGS

FIGS. 1-12 are graphs showing the performance of cells according to the invention.

DESCRIPTION OF PREFERRED FEATURES

Mixtures and Doped Materials

Figure 1:
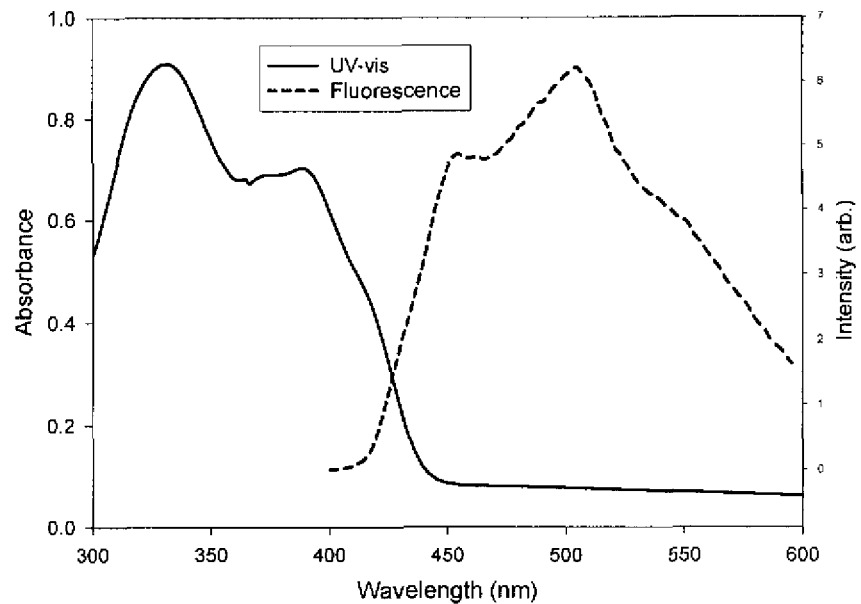

Compounds of the formula are as set out above may be mixed or doped with a range of materials for a range of purposes.

Where they are to serve as electron transfer layers they may be doped with low work function metals e.g. Li, Cs, K, Ca, Ba or complexes thereof e.g. by exposure of the compound in vacuo to vapour of the metal with which the compound is desired to be doped. For example US-A-2006/0079004 (Werner et al, the disclosure of which is incorporated herein by reference) explains that Cs is commonly used because Cs doped organic semiconductors exhibit relatively high stability. Doping by exposure of the organic semiconductor to Cs can be carried out at moderate temperatures about 300° C. using a GaCs alloy e.g. $Ga_7Cs_{11}$. They may also be mixed or doped with complexes e.g quinolates.

Aromatic and heteroaromatic compounds of the formula set out above e.g. phenanthroline compounds may be mixed with other electron transport materials. Kulkarni et al., *Chem. Mater.* 2004, 16, 4556-4573 (the contents of which are incorporated herein by reference) have reviewed the literature concerning electron transport materials (ETMs) used to enhance the performance of organic light-emitting diodes (OLEDs). In addition to a large number of organic materials with which the present compounds can be mixed they discuss metal chelates, with which the present compounds may additionally or alternatively be mixed including aluminium quinolate, which they explain remains the most widely studied metal chelate owing to its superior properties such as high EA (~−3.0 eV; measured by the present applicants as −2.9 eV) and IP (~−5.95 eV; measured by the present applicants as about −5.7 eV), good thermal stability (Tg ~172° C.) and ready deposition of pinhole-free thin films by vacuum evaporation. Aluminium quinolate remains a preferred material both for use as a host to be doped with various fluorescent materials to provide an electroluminescent layer and for use as an electron transport layer. More recently zirconium and hafnium quinolates have been disclosed as electron transport materials, see PCT/GB2007/050737 (Kathirgamanathan et al.) the contents of which are incorporated herein by reference, and the compounds whose formulae are set out above may also be mixed with zirconium or hafnium quinolate. There may also be used e.g. azole compounds such as 2-(4-biphenyl)-5-(4-t-butylphenyl)-1,3,4-oxadiazole (PBD) and 3-(4-biphenylyl)-4-phenyl-5-(4-t-butylphenyl)-1,2,4-triazole (TAZ); phenanthrolines such as 4,7-diphenyl-1,10-phenanthroline (DPA) and 2,9-dimethyl-4,7-diphenyl-1,10-phenanthroline (DDPA); and mixtures thereof.

Compounds of the formula are as set out above may also be mixed any of the compounds claimed in our International application [Case EL,073-PCT] also filed this day, the contents of which are incorporated herein by reference. Such compounds are of the formula

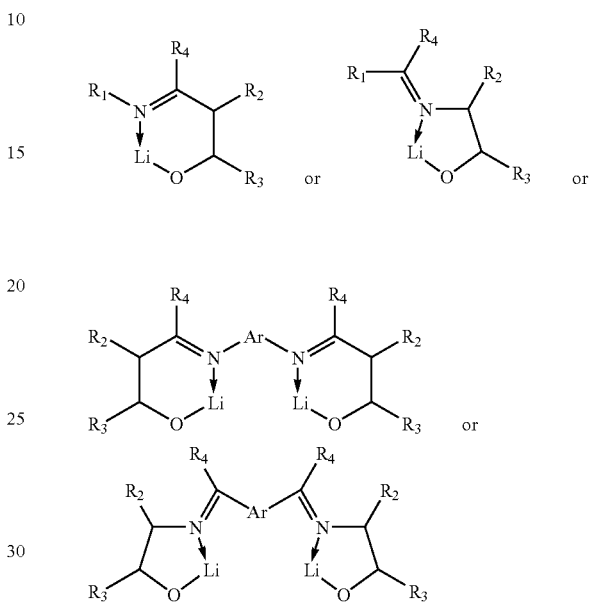

wherein $R_1$ is a 1-5 ring aryl (including polycyclic), aralkyl or heteroaryl group which may be substituted with one or more $C_1$-$C_4$ alkyl, alkoxy or cyano;

$R_2$ and $R_3$ together form a 1-5 ring aryl (including polycyclic), aralkyl or heteroaryl group which may be substituted with $C_1$-$C_4$ alkyl, alkoxy or cyano;

$R_4$ is hydrogen, $C_1$-$C_4$ alkyl or aryl; and

Ar is monocyclic, bicyclic or tricyclic aryl or heteroaryl which may be substituted with one or more $C_1$-$C_4$-alkyl or alkoxy groups, or an oligomer thereof. A preferred sub-genus of compounds is of formula

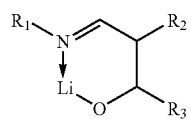

wherein $R_1$ is phenyl or phenyl substituted with one or more $C_1$-$C_4$ alkyl groups and $R_2$ and $R_3$ together form phenyl or phenyl substituted by one or more $C_1$-$C_4$ alkyl groups.

Compounds of the above formula in which $R_4$ is hydrogen may be made by reacting a primary aromatic or heteroaromatic amine with an aromatic or heteroaromatic aldehyde to form a Schiff base, followed by reaction of the Schiff base with a lithium compound e.g. a lithium alkoxide e.g. lithium t-butoxide. Compounds of the above formula in which $R_4$ is alkyl, aryl or heteroaryl may be made similarly starting from a secondary aromatic or heteroaromatic amine.

Vacuum sublimable compounds within the above genus include

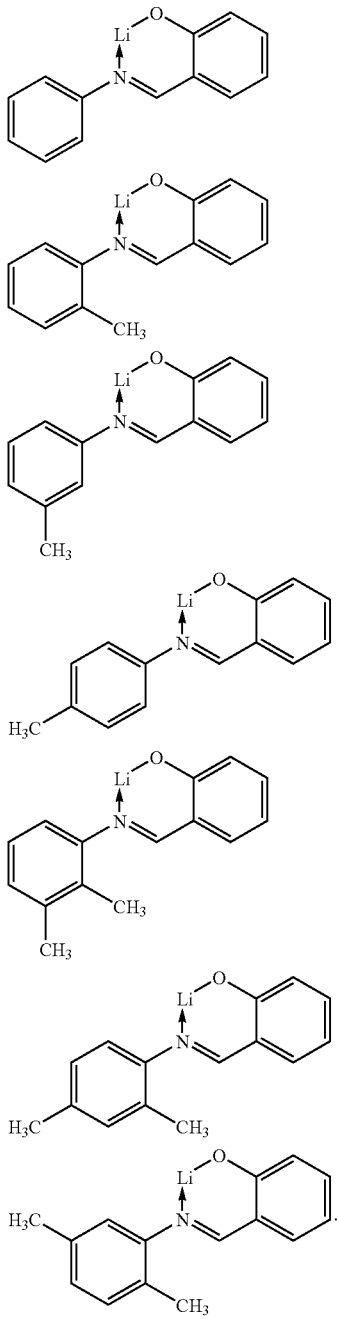

Other compounds which are solution-processable include the following:

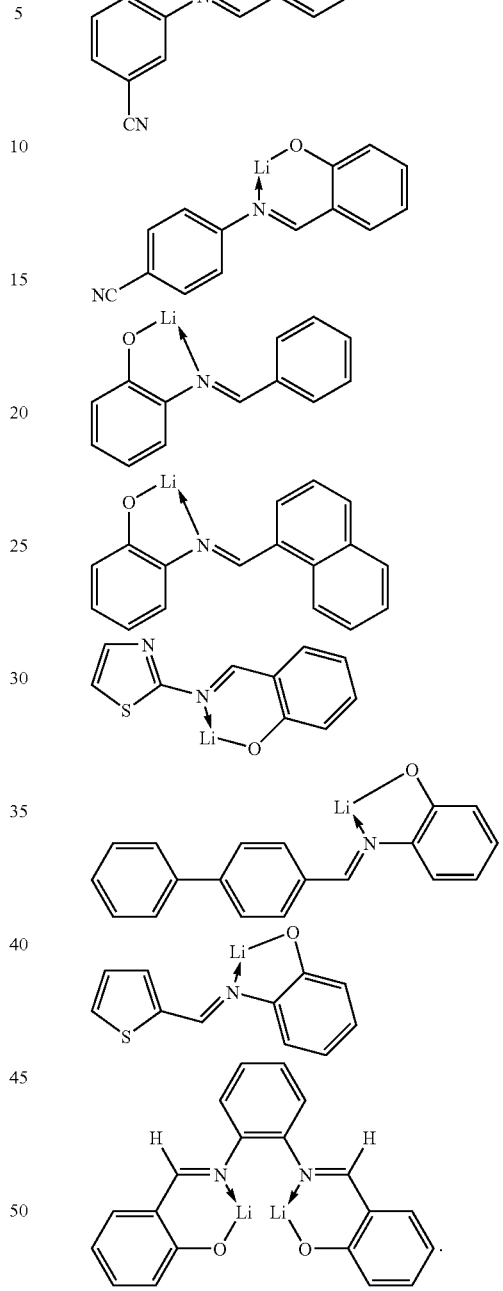

When incorporated into electroluminescent layers, a phenanthroline compound of the formula set out above may be mixed or doped with a fluorescent material or with a phosphorescent material. Such materials are reviewed below in relation to the electroluminescent layer.

Cell Structure

The OLEDs of the invention are useful inter alia in flat panel displays and typically comprise an anode and a cathode between which is sandwiched a multiplicity of thin layers including an electroluminescent layer, electron injection and/or transport layer(s), hole injection and/or transport layer(s) and optionally ancillary layers. The layers are typically built up by successive vacuum vapour deposition operations, although it may be convenient to form one or more of the layers e.g. the hole injection and hole transport layers by other methods e.g. spin coating or ink jet printing.

A typical device comprises a transparent substrate on which are successively formed an anode layer, a hole injector (buffer) layer, a hole transport layer, an electroluminescent layer, an electron transport layer, an electron injection layer and an anode layer which may in turn be laminated to a second transparent substrate. Top emitting OLED's are also possible in which an aluminium or other metallic substrate carries an ITO layer, a hole injection layer, a hole transport layer, an electroluminescent layer, an electron transport layer, an electron injection layer and an ITO or other transparent cathode, light being emitted through the cathode. A further possibility is an inverted OLED in which a cathode of aluminium or aluminium alloyed with a low work function metal carries successively an electron injection layer, an electron transport layer, an electroluminescent layer, a hole transport layer, a hole injection layer and an ITO or other transparent conductive anode, emission of light being through the anode. If desired a hole blocking layer may be inserted e.g. between the electroluminescent layer and the electron transport layer. There may also be incorporated a layer of a reflectivity influencing material e.g. copper quinolate, vanadyl oxyquinolate or vanadyl tetraphenoxy phthalocyanine e.g. as described in WO 2007/052083 (Kathirgamanathan et al.) the contents of which are incorporated herein by reference.

OLEDs of the invention include small molecule OLEDs, polymer light emitting diodes (p-OLEDs), OLEDs that emit light by fluorescence, OLEDs that emit light by phosphorescence (PHOLEDs) and OLEDs that emit light by ion fluorescence (rare earth complexes) and include single-colour or multi-colour active or passive matrix displays.

The front and/or rear plates of an OLED may be provided on front and/or rear surfaces with microlenses or microlens arrays e.g. an array of microlenses of organic polymer (e.g. polymethyl methacrylate) printed onto an OLED substrate or plate e.g. a substrate or plate to form a front plate of an OLED, see e.g. Sun et al., Organic light emitting devices with enhanced outcoupling via microlenses fabricated by imprint lithography, *J. Appl. Phys.* 100, 073106 (2006) and WO 2003/007663 (Moler et al., Princeton). Prismatic and lenticular films are available from Microsharp Corporation Limited of Watchfield, Oxfordshire and microlens and prismatic sheeting is available from 3M Corporation.

There may be employed conducting substrates: ITO/glass, transparent metal coatings/glass, ATO, InZnO/glass and on plastics substrates. Conducting polymer coated plastics and glass may be used, for example, as anodes.

Anode

In many embodiments the anode is formed by a layer of tin oxide or indium tin oxide coated onto glass or other transparent substrate. Other materials that may be used include antimony tin oxide and indium zinc oxide. As regards substrates, rigid or flexible transparent plastics materials may be used, preferably materials which are dimensionally stable, impermeable to water (including water vapour) of relatively high Tg. PEN is a preferred material, other materials that may be used including PES, PEEK and PET. The plastics may be coated with a conductive film and may also have a barrier coating to improve resistance to moisture and hence improve service life.

Hole Injection Materials

A single layer may be provided between the anode and the electroluminescent material, but in many embodiments there are at least two layers one of which is a hole injection layer (buffer layer) and the other of which is a hole transport layer, the two layer structure offering in some embodiments improved stability and device life (see U.S. Pat. No. 4,720,432 (VanSlyke et al., Kodak). The hole injection layer may serve to improve the film formation properties of subsequent organic layers and to facilitate the injection of holes into the hole transport layer.

Suitable materials for the hole injection layer which may be of thickness e.g. 0.1-200 nm depending on material and cell type include hole-injecting porphyrinic compounds—see U.S. Pat. No. 4,356,429 (Tang, Eastman Kodak) e.g. zinc phthalocyanine copper phthalocyanine and ZnTpTP, whose formula is set out below:

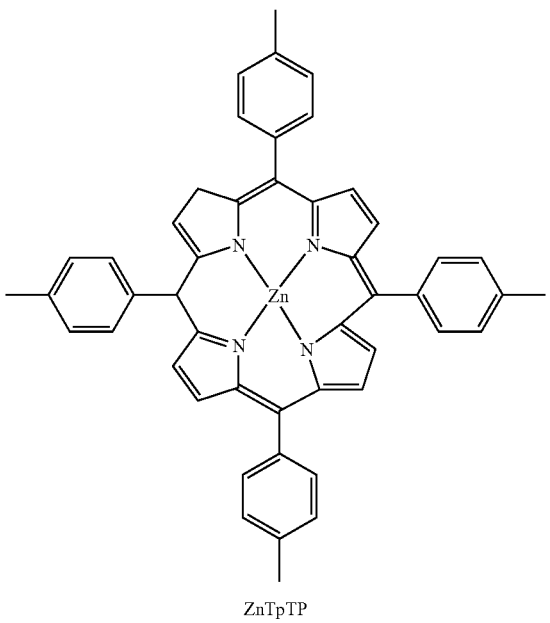

ZnTpTP

Particularly good device efficiencies, turn/on voltages and/or lifetimes may be obtained where the hole injection layer is ZnTpTP and the electron transport layer comprises 2,9-Bis (2-thiophen-2-yl-vinyl)-[1,10] phenanthroline both when the host material for the electroluminescent layer is an organic complex e.g. a metal quinolate such as aluminium quinolate and when the host material is an organic small molecule material.

The hole injection layer may also be a fluorocarbon-based conductive polymer formed by plasma polymerization of a fluorocarbon gas—see U.S. Pat. No. 6,208,075 (Hung et al; Eastman Kodak), a triarylamine polymer—see EP-A-0891121 (Inoue et al., TDK Corporation) or a phenylenediamine derivative—see EP-A-1029909 (Kawamura et al., Idemitsu).

Hole-Transport Materials

Hole transport layers which may be used are preferably of thickness 20 to 200 nm.

One class of hole transport materials comprises polymeric materials that may be deposited as a layer by means of spin coating. Such polymeric hole-transporting materials include poly(N-vinylcarbazole) (PVK), polythiophenes, polypyrrole, and polyaniline. Other hole transporting materials are conjugated polymers e.g. poly (p-phenylenevinylene) (PPV) and copolymers including PPV. Other preferred polymers are: poly(2,5 dialkoxyphenylene vinylenes e.g. poly (2-methoxy-5-(2-methoxypentyloxy-1,4-phenylene vinylene), poly(2-methoxypentyloxy)-1,4-phenylenevinylene), poly(2-methoxy-5-(2-dodecyloxy-1,4-phenylenevinylene) and other poly(2,5 dialkoxyphenylenevinylenes) with at least one of the alkoxy groups being a long chain solubilising alkoxy group; polyfluorenes and oligofluorenes; polyphenylenes and oligophenylenes; polyanthracenes and oligoanthracenes; and polythiophenes and oligothiophenes.

A further class of hole transport materials comprises sublimable small molecules. For example, aromatic tertiary amines provide a class of preferred hole-transport materials, e.g. aromatic tertiary amines including at least two aromatic tertiary amine moieties (e.g. those based on biphenyl diamine or of a "starburst" configuration), of which the following are representative:

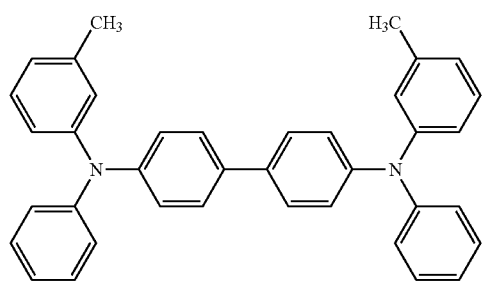

TPD Tg(° C.) 61
μh (cm²V⁻¹s⁻¹) 1 x 10⁻³

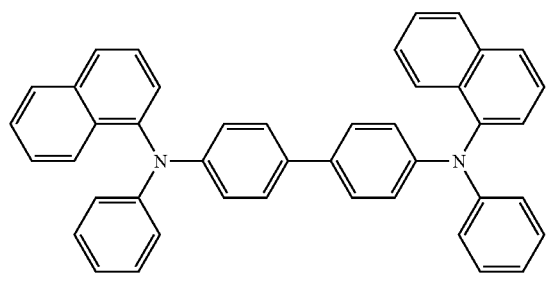

α-NBP Tg(° C.) 98
μh (cm²V⁻¹s⁻¹) 1 x 10⁻⁴

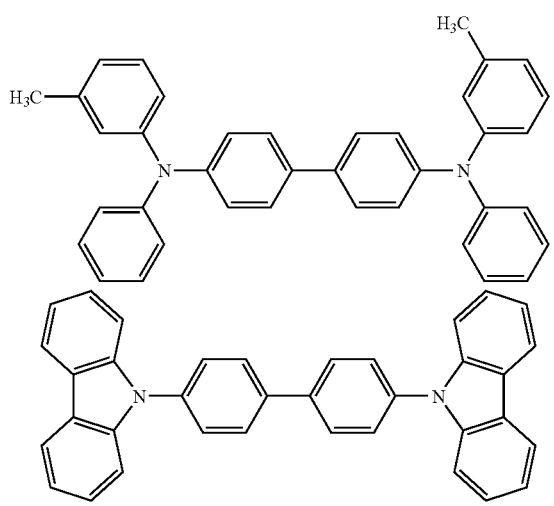

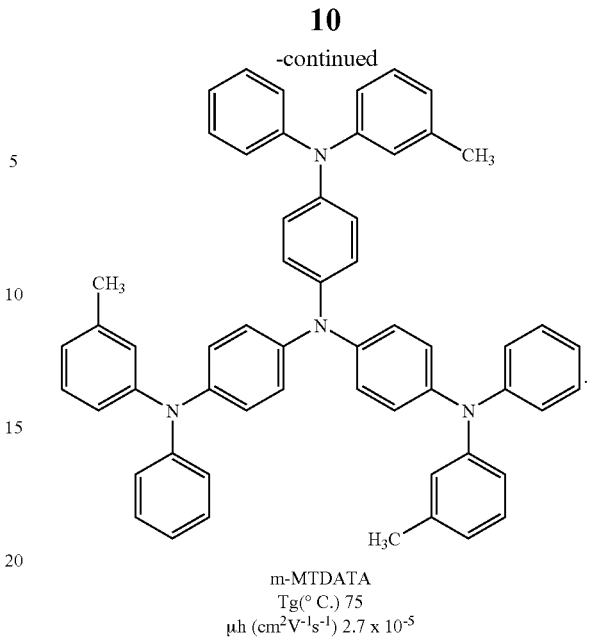

m-MTDATA
Tg(° C.) 75
μh (cm²V⁻¹s⁻¹) 2.7 x 10⁻⁵

It further includes spiro-linked molecules which are aromatic amines e.g. spiro-TAD (2,2',7,7'-tetrakis-(diphenylamino)-spiro-9,9'-bifluorene).

A further class of small molecule hole transport materials is disclosed in WO 2006/061594 (Kathirgamanathan et al) and is based on diamino dianthracenes. Typical compounds include:
9-(10-(N-(naphthalen-1-yl)-N-phenylamino)anthracen-9-yl)-N-(naphthalen-1-yl)-N-phenylanthracen-10-amine;
9-(10-(N-biphenyl-N-2-m-tolylamino)anthracen-9-yl)-N-biphenyl-N-2-m-tolylamino-anthracen-10-amine; and
9-(10-(N-phenyl-N-m-tolylamino)anthracen-9-yl)-N-phenyl-N-m-tolylanthracen-10-amine.

Electroluminescent Materials

In principle any electroluminescent material may be used, including molecular solids which may be fluorescent dyes e.g. perylene dyes, metal complexes e.g. Alq₃, Ir(III)L₃, rare earth chelates e.g. Tb(III) complexes, dendrimers and oligomers e.g. sexithiophene, or polymeric emissive materials. The electroluminescent layer may comprise as luminescent material a metal quinolate, iridium, ruthenium, osmium, rhodium, iridium, palladium or platinum complex, a boron complex or a rare earth complex.

One preferred class of electroluminescent materials comprises host materials doped with dyes which may be fluorescent, phosphorescent or ion-phosphorescent (rare earth). The term "electroluminescent device" includes electrophosphorescent devices.

Preferably the host is doped with a minor amount of a fluorescent material as a dopant, preferably in an amount of 0.01 to 25% by weight of the doped mixture. As discussed in U.S. Pat. No. 4,769,292 (Tang et al., Kodak), the contents of which are included by reference, the presence of the fluorescent material permits a choice from amongst a wide latitude of wavelengths of light emission. In particular, as disclosed in U.S. Pat. No. 4,769,292 by blending with the organo metallic complex a minor amount of a fluorescent material capable of emitting light in response to hole-electron recombination, the hue of the light emitted from the luminescent zone, can be modified. In theory, if a host material and a fluorescent material could be found for blending which have exactly the same affinity for hole-electron recombination, each material should emit light upon injection of holes and electrons in the luminescent zone. The perceived hue of light emission would be the visual integration of both emissions. However, since imposing such a balance of host material and fluorescent materials is limiting, it is preferred to choose the fluorescent material so that it provides the favoured sites for light emission. When only a small proportion of fluorescent material providing favoured sites for light emission is present, peak intensity wavelength emissions typical of the host material can be entirely eliminated in favour of a new peak intensity wavelength emission attributable to the fluorescent material.

While the minimum proportion of fluorescent material sufficient to achieve this effect varies, in no instance is it necessary to employ more than about 10 mole percent fluorescent material, based of host material and seldom is it necessary to employ more than 1 mole percent of the fluorescent material. On the other hand, limiting the fluorescent material present to extremely small amounts, typically less than about $10^{-3}$ mole percent, based on the host material, can result in retaining emission at wavelengths characteristic of the host material. Thus, by choosing the proportion of a fluorescent material capable of providing favoured sites for light emission, either a full or partial shifting of emission wavelengths can be realized. This allows the spectral emissions of the EL devices to be selected and balanced to suit the application to be served. In the case of fluorescent dyes, typical amounts are 0.01 to 5 wt %, for example 2-3 wt %. In the case of phosphorescent dyes typical amounts are 0.1 to 15 wt %. In the case of ion phosphorescent materials typical amounts are 0.01-25 wt % or up to 100 wt %.

Choosing fluorescent materials capable of providing favoured sites for light emission, necessarily involves relating the properties of the fluorescent material to those of the host material. The host can be viewed as a collector for injected holes and electrons with the fluorescent material providing the molecular sites for light emission. One important relationship for choosing a fluorescent material capable of modifying the hue of light emission when present in the host is a comparison of the reduction potentials of the two materials. The fluorescent materials demonstrated to shift the wavelength of light emission have exhibited a less negative reduction potential than that of the host. Reduction potentials, measured in electron volts, have been widely reported in the literature along with varied techniques for their measurement. Since it is a comparison of reduction potentials rather than their absolute values which is desired, it is apparent that any accepted technique for reduction potential measurement can be employed, provided both the fluorescent and host reduction potentials are similarly measured. A preferred oxidation and reduction potential measurement techniques is reported by R. J. Cox, *Photographic Sensitivity*, Academic Press, 1973, Chapter 15.

A second important relationship for choosing a fluorescent material capable of modifying the hue of light emission when present in the host is a comparison of the band-gap potentials of the two materials. The fluorescent materials demonstrated to shift the wavelength of light emission have exhibited a lower band gap potential than that of the host. The band gap potential of a molecule is taken as the potential difference in electron volts (eV) separating its ground state and first singlet state. Band gap potentials and techniques for their measurement have been widely reported in the literature. The band gap potentials herein reported are those measured in electron volts (eV) at an absorption wavelength which is bathochromic to the absorption peak and of a magnitude one tenth that of the magnitude of the absorption peak. Since it is a comparison of band gap potentials rather than their absolute values which is desired, it is apparent that any accepted technique for band gap measurement can be employed, provided both the fluorescent and host band gaps are similarly measured. One illustrative measurement technique is disclosed by F. Gutman and L. E. Lyons, *Organic Semiconductors*, Wiley, 1967, Chapter 5.

With host materials which are themselves capable of emitting light in the absence of the fluorescent material, it has been observed that suppression of light emission at the wavelengths of emission characteristics of the host alone and enhancement of emission at wavelengths characteristic of the fluorescent material occurs when spectral coupling of the host and fluorescent material is achieved. By "spectral coupling" it is meant that an overlap exists between the wavelengths of emission characteristic of the host alone and the wavelengths of light absorption of the fluorescent material in the absence of the host. Optimal spectral coupling occurs when the emission wavelength of the host is within ±25 nm of the maximum absorption of the fluorescent material alone. In practice advantageous spectral coupling can occur with peak emission and absorption wavelengths differing by up to 100 nm or more, depending on the width of the peaks and their hypsochromic and bathochromic slopes. Where less than optimum spectral coupling between the host and fluorescent materials is contemplated, a bathochromic as compared to a hypsochromic displacement of the fluorescent material produces more efficient results.

Useful fluorescent materials are those capable of being blended with the host and fabricated into thin films satisfying the thickness ranges described above forming the luminescent zones of the EL devices of this invention. While crystalline organometallic complexes do not lend themselves to thin film formation, the limited amounts of fluorescent materials present in the host permit the use of fluorescent materials which are alone incapable of thin film formation. Preferred fluorescent materials are those which form a common phase with the host. Fluorescent dyes constitute a preferred class of fluorescent materials, since dyes lend themselves to molecular level distribution in the host. Although any convenient technique for dispersing the fluorescent dyes in the host can be used preferred fluorescent dyes are those which can be vacuum vapour deposited along with the host materials.

One class of host materials comprises metal complexes e.g. metal quinolates such as lithium quinolate, aluminium quinolate, titanium quinolate, zirconium quinolate or hafnium quinolate which may be doped with fluorescent materials or dyes as disclosed in patent application WO 2004/058913.

In the case of quinolates e.g. aluminium quinolate:

(a) the compounds below, for example, can serve as red dopants:

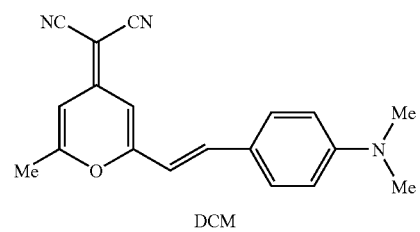

DCM

-continued

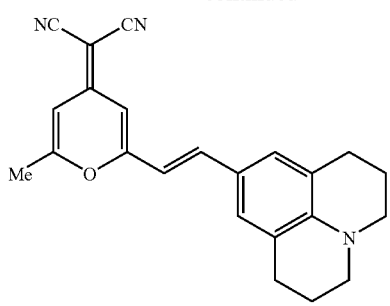

DCJT

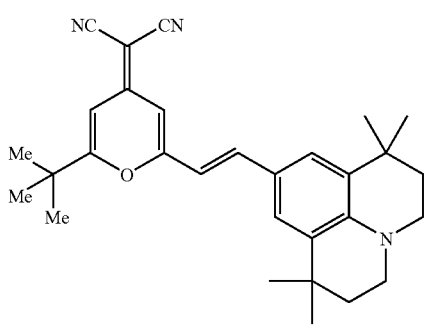

DCJTi

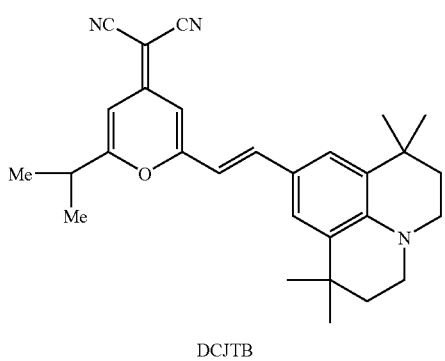

DCJTB (b) the compounds below, for example can serve as green dopants:

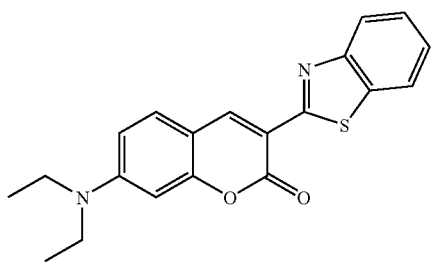

-continued

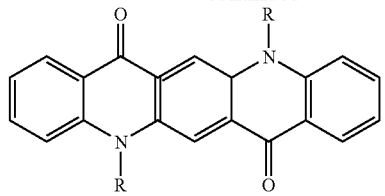

wherein R is $C_1$-$C_4$ alkyl, monocyclic aryl, bicycic aryl, monocyclic heteroaryl, bicyclic heteroaryl, aralkyl or thienyl, preferably phenyl; and (c) for biphenyloxy aluminium bis-quinolate (BAlQ$_2$) or aluminium quinolate the compounds perylene and 9-(10-(N-(naphthalen-8-yl)-N-phenylamino)anthracen-9-yl)-N-(naphthalen-8-yl)-N-phenylanthracen-10-amine can serve as a blue dopants.

Another preferred class of hosts is small molecules incorporating conjugated aromatic systems with e.g. 4-10 aryl or heteroaryl rings which may bear substituents e.g. alkyl (especially methyl), alkoxy and fluoro and which may also be doped with fluorescent materials or dyes.

An example of a system of the above kind is a blue-emitting material based on the following compound (Compound H) as host

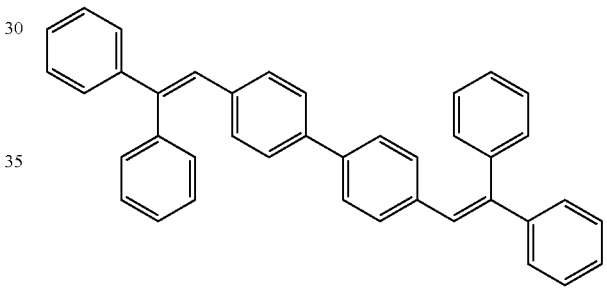

and perylene or 9-(10-(N-(naphthalen-8-yl)-N-phenylamino)anthracen-9-yl)-N-(naphthalen-8-yl)-N-phenylanthracen-10-amine a s dopant. Further examples of host materials which are small aromatic molecules are shown below:

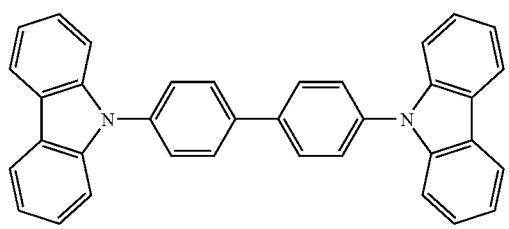

CBP

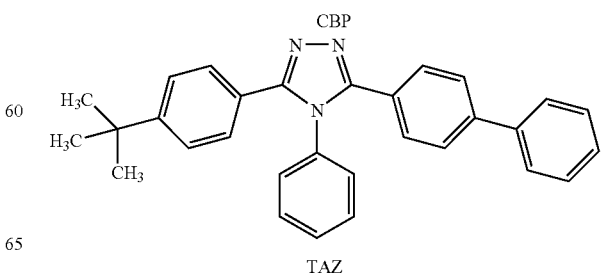

TAZ

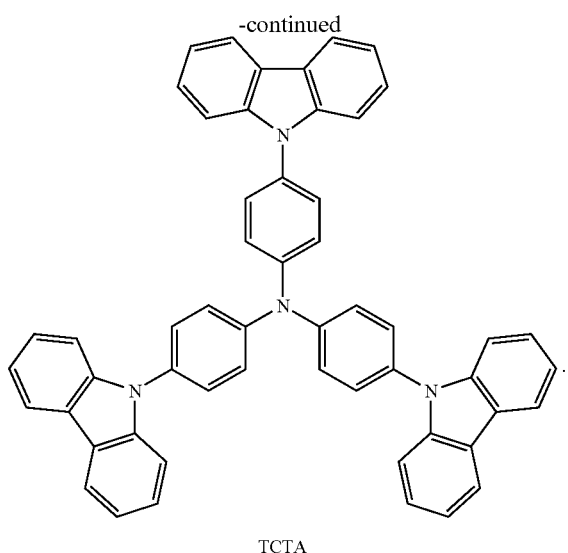

TCTA 2,9-Bis(2-thiophen-2-yl-vinyl)-[1,10]phenanthroline may, as explained above, may be used as host in the electroluminescent layer or may be present on its own.

Blue-emitting materials may be based on an organic host (e.g. a conjugated aromatic compound as indicated above) and diarylamine anthracene compounds disclosed in WO 2006/090098 (Kathirgamanathan et al.) as dopants. For example, CBP may be doped with blue-emitting substituted anthracenes inter alia
9,10-bis(-4-methylbenzyl)-anthracene,
9,10-bis-(2,4-dimethylbenzyl)-anthracene,
9,10-bis-(2,5-dimethylbenzyl)-anthracene,
1,4-bis-(2,3,5,6-tetramethylbenzyl)-anthracene,
9,10-bis-(4-methoxybenzyl)-anthracene,
9,10-bis-(9H-fluoren-9-yl)-anthracene,
2,6-di-t-butylanthracene,
2,6-di-t-butyl-9,10-bis-(2,5-dimethylbenzyl)-anthracene,
2,6-di-t-butyl-9,10-bis-(naphthalene-1-ylmethyl)-anthracene.

Further blue-emitting materials may employ TCTA as host and it may be doped with the blue phosphorescent materials set out below, see WO 2005/080526 (Kathirgamanathan et al.):

Blue Phosphorescent Materials

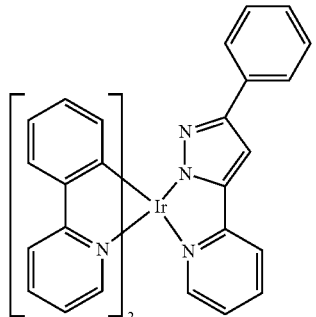

λmax 495nm (DCM)

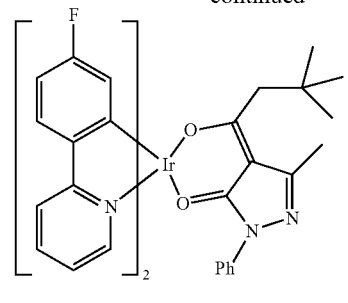

λmax 493nm (DCM)

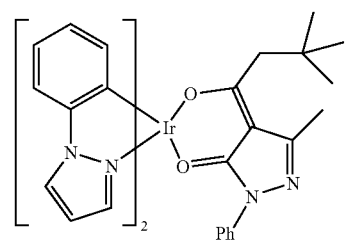

λmax 485nm (DCM)

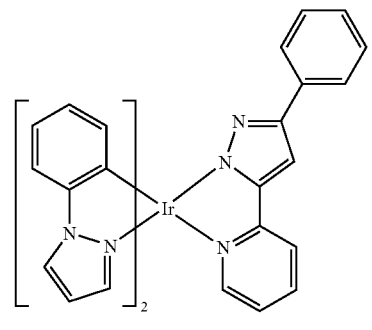

λmax 485nm (DCM)

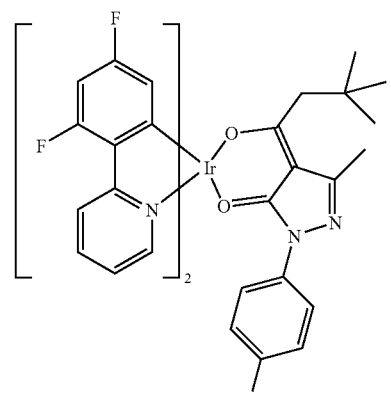

λmax 484nm (DCM)

17
-continued
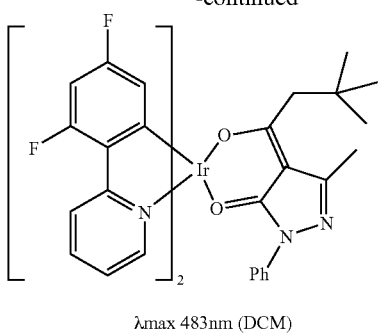
λmax 483nm (DCM)
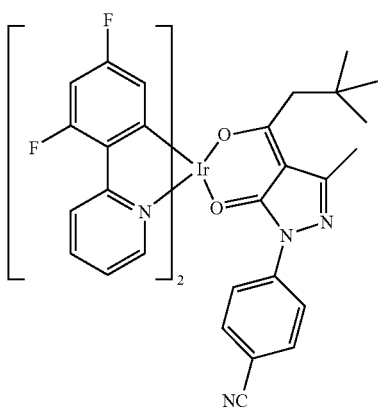
λmax 480nm (DCM)
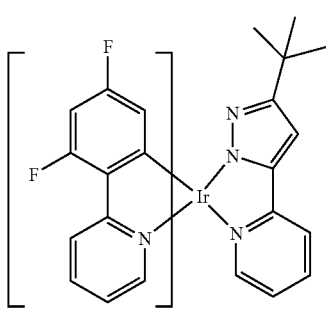
λmax 479nm (DCM)
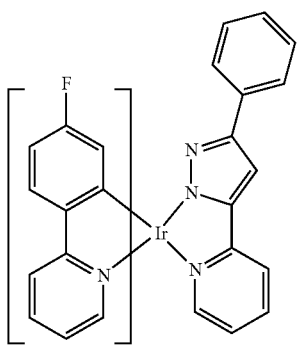
λmax 477nm (DCM)
18
-continued
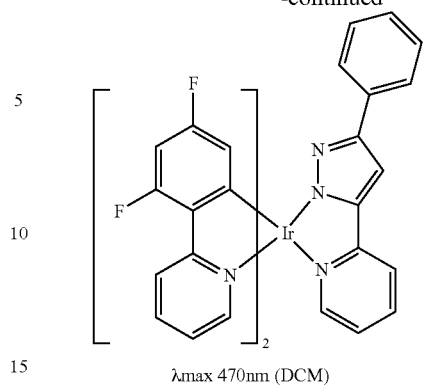
λmax 470nm (DCM)
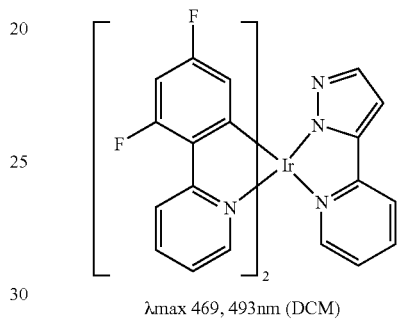
λmax 469, 493nm (DCM)
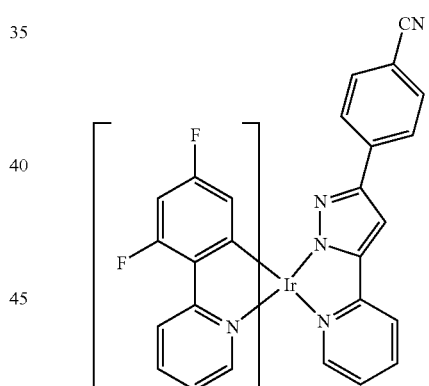
λmax 468nm (DCM)
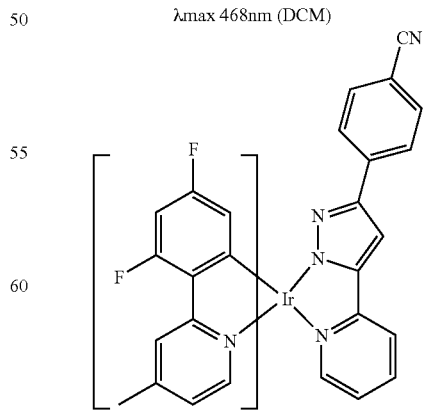
λmax 462nm (DCM)

Examples of green phosphorescent materials that may be employed with CBP or TAZ are set out below (see WO 2005/080526):
Green Phosphorescent Materials
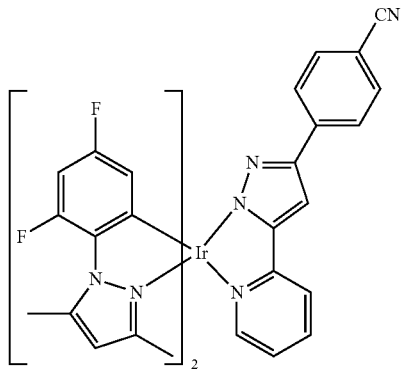
λmax 502 nm (DCM)
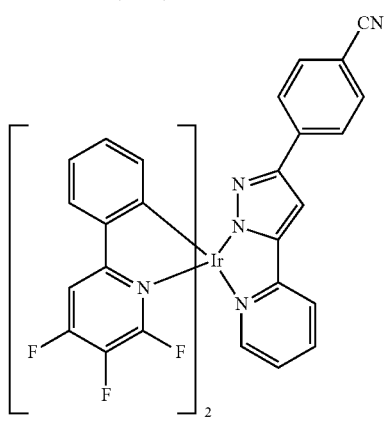
λmax 509 nm (DCM)
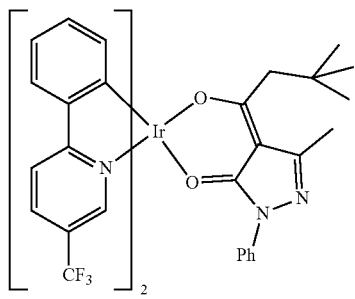
λmax 520 nm (DCM)
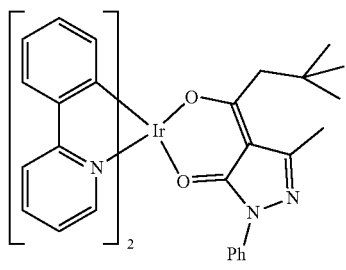
λmax 526 nm (DCM)
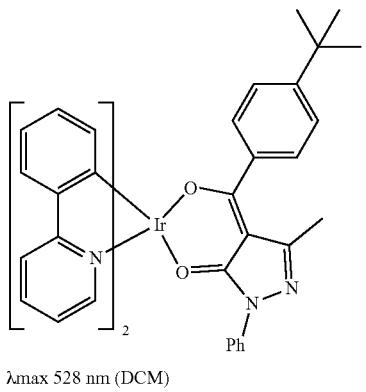
λmax 528 nm (DCM)
Examples of red phosphorescent materials that may be employed with CBP or TAZ are set out below (see WO 2005/080526):
Red Phosphorescent Materials
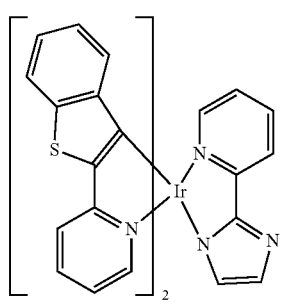
λmax 596 nm (DCM)
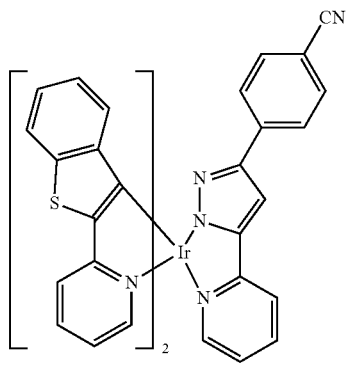
λmax 596 nm (DCM)
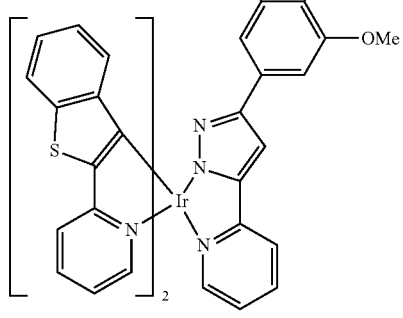
λmax 597 nm (DCM)

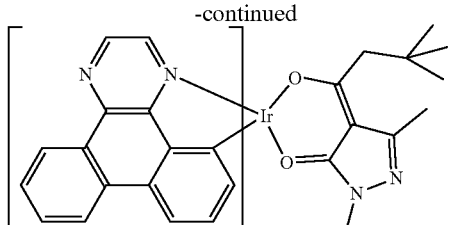

λmax 600 nm (DCM)

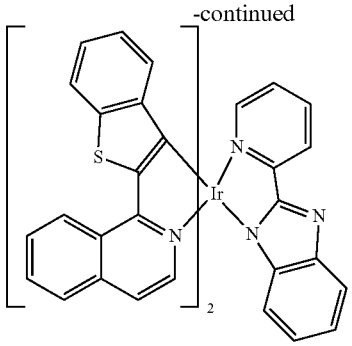

λmax 682 nm (DCM)

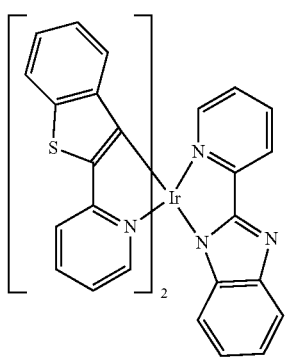

λmax 604 nm (DCM)

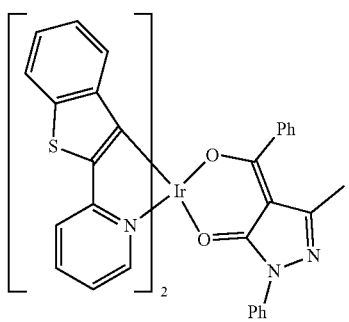

λmax 614 nm (DCM)

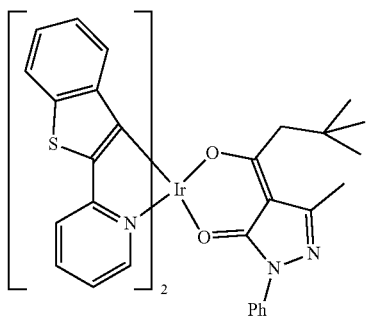

λmax 615 nm (DCM)

As further dopants, fluorescent laser dyes are recognized to be particularly useful fluorescent materials for use in the organic EL devices of this invention. Dopants which can be used include diphenylacridine, coumarins, perylene and their derivatives. Useful fluorescent dopants are disclosed in U.S. Pat. No. 4,769,292. One class of preferred dopants is coumarins. The following are illustrative fluorescent coumarin dyes known to be useful as laser dyes:

FD-1 7-Diethylamino-4-methylcoumarin,
FD-2 4,6-Dimethyl-7-ethylaminocoumarin,
FD-3 4-Methylumbelliferone,
FD-4 3-(2'-Benzothiazolyl)-7-diethylaminocoumarin,
FD-5 3-(2'-Benzimidazolyl)-7-N,N-diethylaminocoumarin,
FD-6 7-Amino-3-phenylcoumarin,
FD-7 3-(2'-N-Methylbenzimidazolyl)-7-N,N-diethylaminocoumarin,
FD-8 7-Diethylamino-4-trifluoromethylcoumarin,
FD-9 2,3,5,6-1H,4H-Tetrahydro-8-methylquinolazino[9,9a,1-gh]coumarin,
FD-10 Cyclopenta[c]julolindino[9,10-3]-11H-pyran-11-one,
FD-11 7-Amino-4-methylcoumarin,
FD-12 7-Dimethylaminocyclopenta[c]coumarin,
FD-13 7-Amino-4-trifluoromethylcoumarin,
FD-14 7-Dimethylamino-4-trifluoromethylcoumarin,
FD-15 1,2,4,5,3H,6H,10H-Tetrahydro-8-trifluoromethyl[1]benzopyrano[9,9a,1-gh]quinolizin-10-one,
FD-16 4-Methyl-7-(sulfomethylamino)coumarin sodium salt,
FD-17 7-Ethylamino-6-methyl-4-trifluoromethylcoumarin,
FD-18 7-Dimethylamino-4-methylcoumarin,
FD-19 1,2,4,5,3H,6H,10H-Tetrahydro-carbethoxy[1]benzopyrano[9,9a,1-gh]quinolizino-10-one,
FD-20 9-Acetyl-1,2,4,5,3H,6H,10H-tetrahydro[1]benzopyrano[9,9a,1-gh]quinolizino-10-one,
FD-21 9-Cyano-1,2,4,5,3H,6H,10H-tetrahydro[1]benzopyrano[9,9a,1-gh]quinolizino-10-one,
FD22 9-(t-Butoxycarbonyl)-1,2,4,5,3H,6H,10H-tetrahyro[1]-benzopyrano-[9,9a,1-gh]quinolizino-10-one,
FD-23 4-Methylpiperidino[3,2-g]coumarin,
FD-24 4-Trifluoromethylpiperidino[3,2-g]coumarin,
FD-25 9-Carboxy-1,2,4,5,3H,6H,10H-tetrahydro[1]benzopyrano[9,9a,1-gh]quinolizino-10-one,
FD-26 N-Ethyl-4-trifluoromethylpiperidino[3,2-g].

Other dopants include salts of bis benzene sulphonic acid (require deposition by spin-coating rather than sublimation) such as

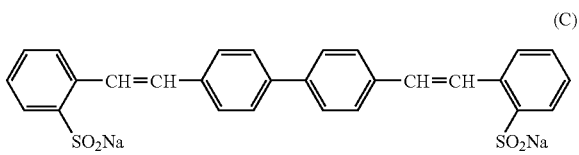
(C)

and perylene and perylene derivatives and dopants. Other dopants are dyes such as the fluorescent 4-dicyanomethylene-4H-pyrans and 4-dicyanomethylene-4H-thiopyrans, e.g. the fluorescent dicyanomethylenepyran and thiopyran dyes. Useful fluorescent dyes can also be selected from among known polymethine dyes, which include the cyanines, complex cyanines and merocyanines (i.e. tri-, tetra- and poly-nuclear cyanines and merocyanines), oxonols, hemioxonols, styryls, merostyryls, and streptocyanines. The cyanine dyes include, joined by a methine linkage, two basic heterocyclic nuclei, such as azolium or azinium nuclei, for example, those derived from pyridinium, quinolinium, isoquinolinium, oxazolium, thiazolium, selenazolium, indazolium, pyrazolium, pyrrolium, indolium, 3H-indolium, imidazolium, oxadiazolium, thiadioxazolium, benzoxazolium, benzothiazolium, benzoselenazolium, benzotellurazolium, benzimidazolium, 3H- or 1H-benzoindolium, naphthoxazolium, naphthothiazolium, naphthoselenazolium, naphthotellurazolium, carbazolium, pyrrolopyridinium, phenanthrothiazolium, and acenaphthothiazolium quaternary salts. Other useful classes of fluorescent dyes are 4-oxo-4H-benz-[d,e]anthracenes and pyrylium, thiapyrylium, selenapyrylium, and telluropyrylium dyes.

Further blue-emitting materials are disclosed in the following patents, applications and publications, the contents of which are incorporated herein by reference:

U.S. Pat. No. 5,141,671 (Bryan, Kodak)—Aluminium chelates containing a phenolato ligand and two 8-quinolinolato ligands.

WO 00/32717 (Kathirgamanathan)—Lithium quinolate which is vacuum depositable, and other substituted quinolates of lithium where the substituents may be the same or different in the 2, 3, 4, 5, 6 and 7 positions and are selected from alky, alkoxy, aryl, aryloxy, sulphonic acids, esters, carboxylic acids, amino and amido groups or are aromatic, polycyclic or heterocyclic groups.

US 2006/0003089 (Kathirgamanathan)—Lithium quinolate made by reacting a lithium alkyl or alkoxide with 8-hydroxyquinoline in acetonitrile.

Misra, http://www.ursi.org/Proceedings/ProcGA05/pdf/D04.5(01720).pdf Blue organic electroluminescent material bis-(2-methyl 8-quinolinolato) (triphenyl siloxy)aluminium (III) vacuum depositable at $1 \times 10^{-5}$ Torr.

WO 03/006573 (Kathirgamanathan et al)—Metal pyrazolones.

WO 2004/084325 (Kathirgamanathan et al)—Boron complexes.

WO 2005/080526 (Kathitgamanathan et al)—Blue phosphorescent iridium-based complexes.

Ma et al., Chem. Comm. 1998, 2491-2492 Preparation and crystal structure of a tetranuclear zinc(II) compound [Zn$_4$O (AID)$_6$] with 7-azaindolate as a bridging ligand. Fabrication of inter alia a single-layer LED by vacuum deposition of this compound (<200° C., $2 \times 10^{-6}$ Ton) onto a glass substrate coated with indium-tin oxide to form a thin homogeneous film was reported.

Further electroluminescent materials which can be used include metal quinolates such as aluminium quinolate, lithium quinolate, titanium quinolate, zirconium quinolate, hafnium quinolate etc.

Many further electroluminescent materials that may be used are disclosed in WO 2004/050793 (pyrazolones), WO 2004/058783 (diiridium metal complexes), WO 2006/016193 (dibenzothiophenyl metal complexes) and WO 2006/024878 (thianthrene metal complexes), see also WO 2006/040593 the contents of which are incorporated herein by reference. Rare earth chelates, in particular may be employed as green and red emitters. Furthermore, there may be used as electroluminescent materials conducting polymers e.g. polyaniline, phenylene vinylene polymers, fluorene homopolymers and copolymers, phenylene polymers, as indicated below:

Conducting Polymers

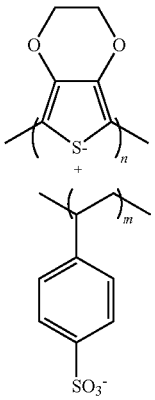

PEDOT-PSS ($\sigma = 1$ S cm$^{-1}$)

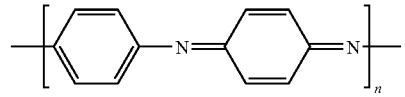

Polyaniline (PANI)($\sigma = 1 - 10$ S cm$^{-1}$)

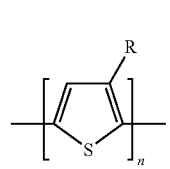 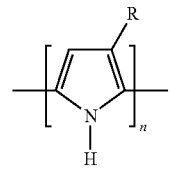

Polythiophene (PT)  Polypyrrole (PPy)
($\sigma = 1 - 500$ S cm$^{-1}$)  ($\sigma = 1 - 100$ S cm$^{-1}$)

Electron Transport Material

As explained, the electron transport material used here consists of or comprises a compound as defined above e.g. 2,9-Bis(2-thiophen-2-yl-vinyl)-[1,10]phenanthroline. Preferably the content of compound as defined above e.g. 2,9-Bis (2-thiophen-2-yl-vinyl)-[1,10]phenanthroline in the ET layer is at least 30 wt %, preferably at least 50 wt %.

Embodiments of the above compounds may be made by condensing a compound of formula

[Phen](CH$_3$)$_n$ wherein n is as defined above with a compound of formula R$_1$CHO in the presence of an acid catalyst e.g. an anhydride of an organic acid.

Electron Injection Material

Any known electron injection material may be used, LiF being typical. Other possibilities include $BaF_2$, $CaF_2$ and $CsF_2$.

Cathode

In many embodiments, aluminium is used as the cathode either on its own or alloyed with elements such as magnesium or silver, although in some embodiments other cathode materials e.g. calcium may be employed. In an embodiment the cathode may comprise a first layer of alloy e.g. Li—Ag, Mg—Ag or Al—Mg closer to the electron injection or electron transport layer and an second layer of pure aluminium further from the electron injection or electron transport layer. Cathode materials may also be on transparent plate materials which may be of glass or may be of plastics which may be rigid or flexible and may be optically transparent As regards plastics substrates, rigid or flexible transparent plastics materials may be used, preferably materials which are dimensionally stable, impermeable to water (including water vapour) of relatively high Tg. PEN is a preferred material, other materials that may be used including PES, PEEK and PET. The plastics may be coated with a conductive film and may also have a barrier coating to improve resistance to moisture which may be encountered under working conditions e.g. atmospheric moisture.

How the invention may be put into effect will now be described with reference to the following examples.

Preparative Methods

Preparation of 2,9-Bis(2-thiophen-2-yl-vinyl)-[1,10]phenanthroline

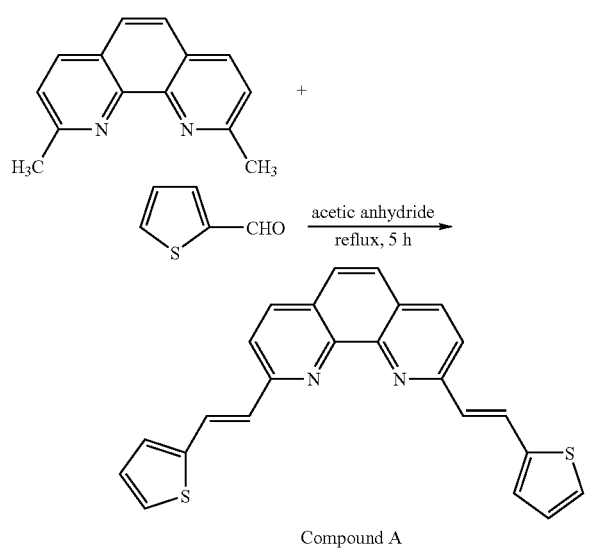

Compound A

Figure 2:
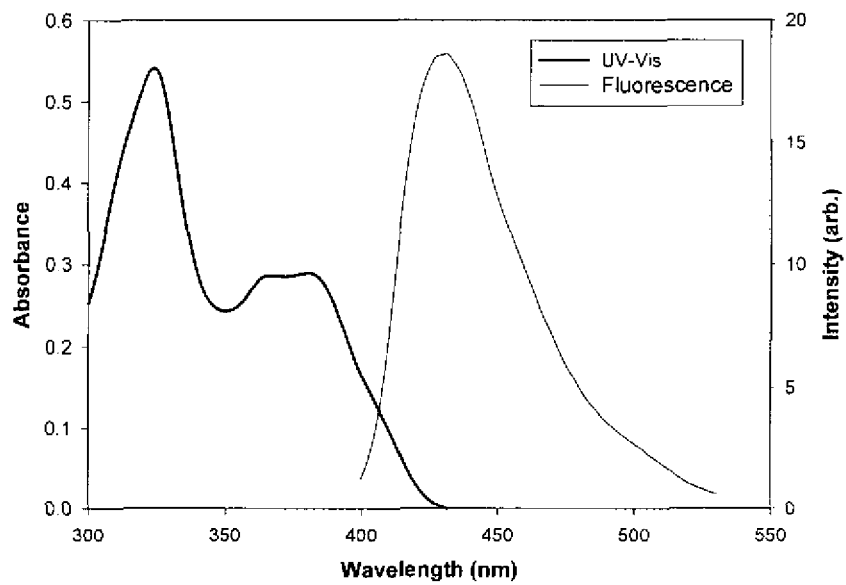
Figure 3:
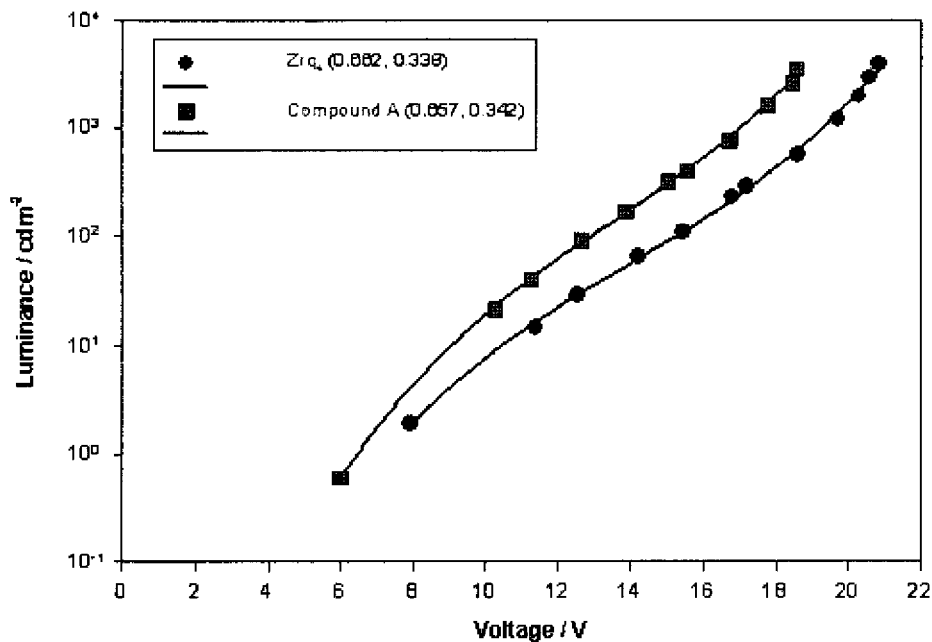
Figure 4:
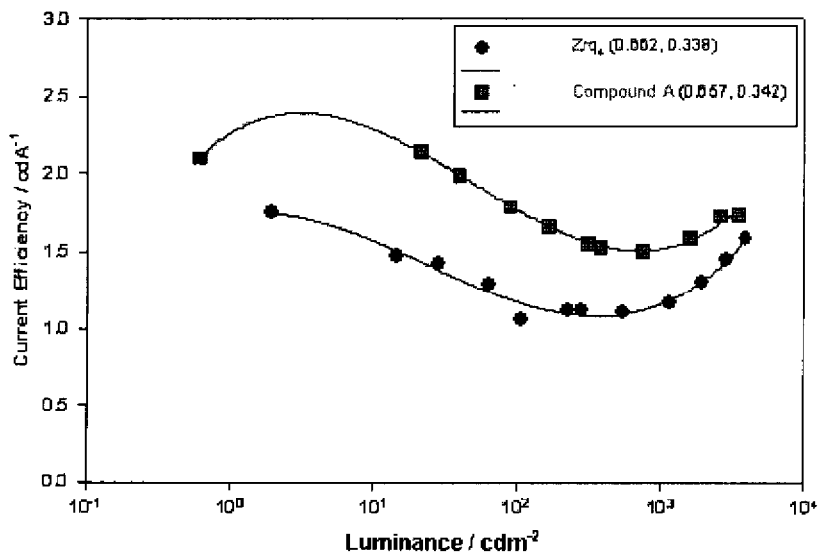
Figure 7:
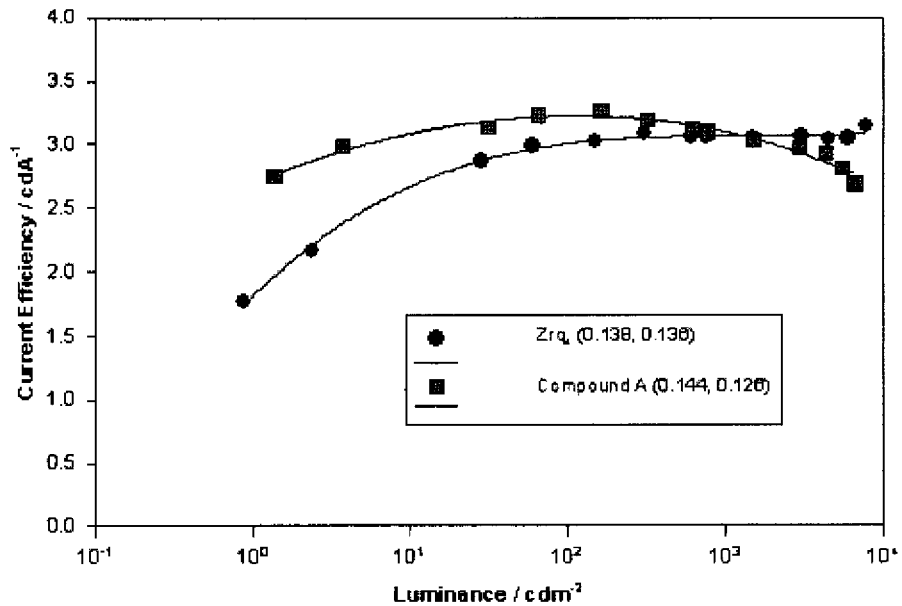
Figure 8:
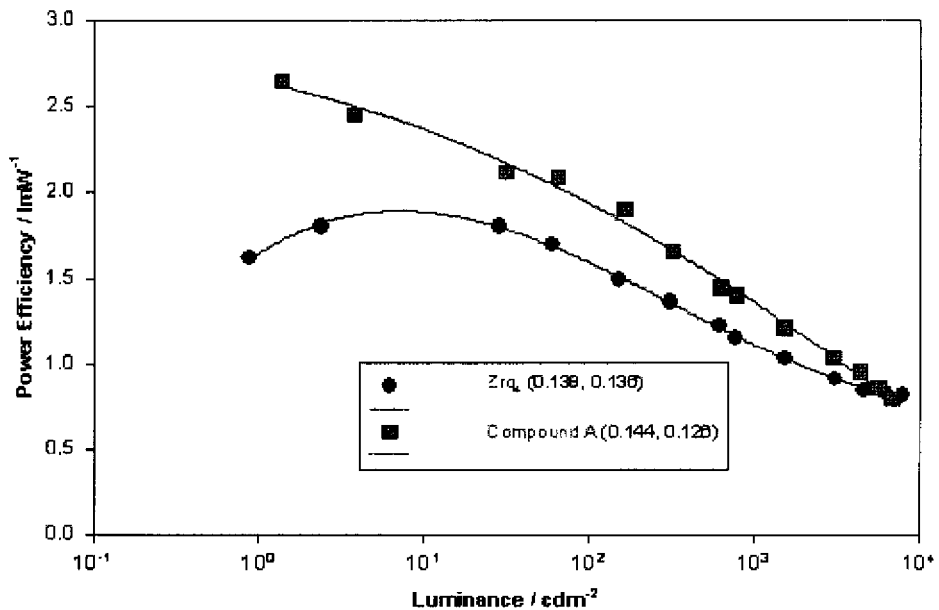
Figure 9:
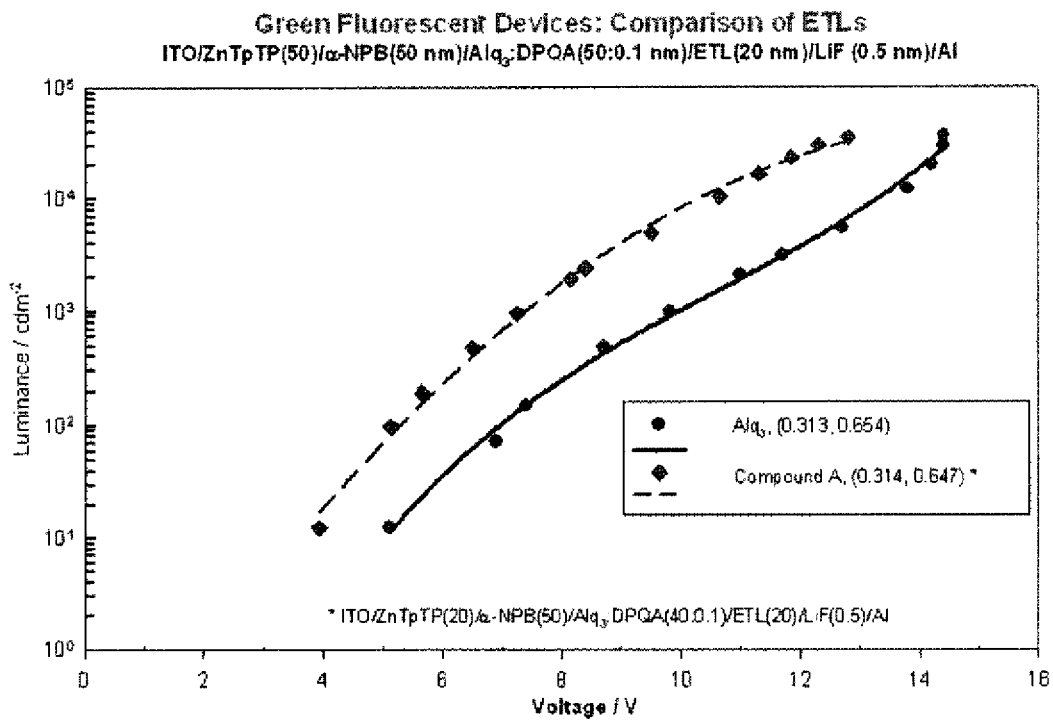
Figure 10:
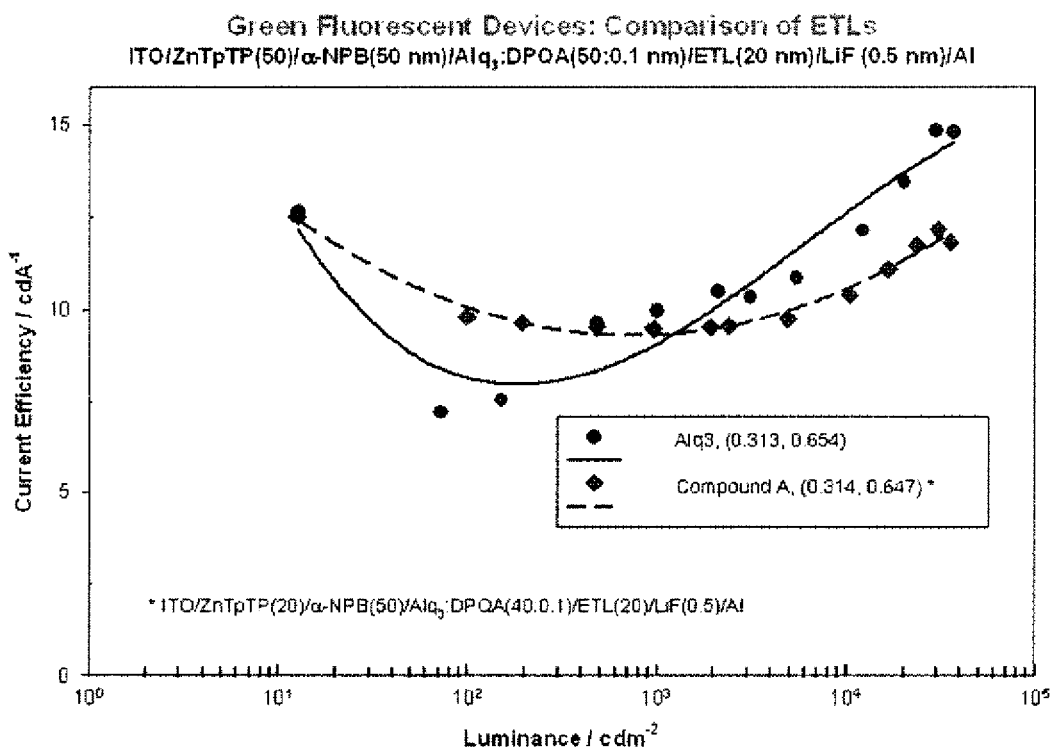
Figure 11:
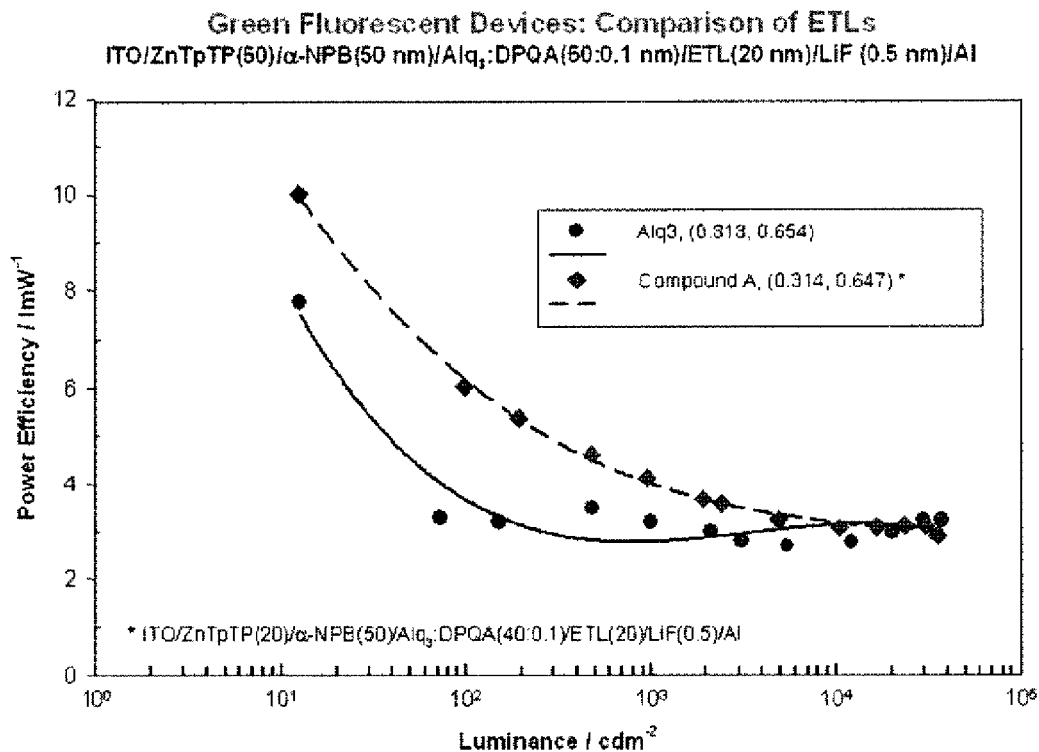
Figure 12:
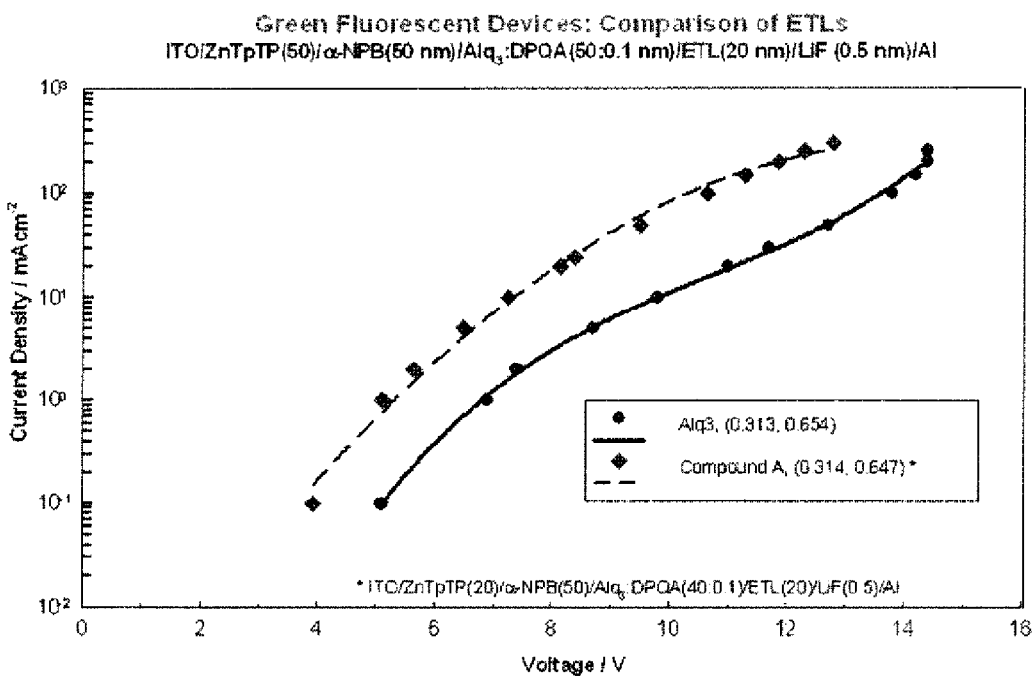

A mixture of 2,9-dimethyl-1,10-phenanthroline (neocuproine hydrate) (10 g, 0.048 mole) and 2-thiophene carboxaldehyde (9.4 ml, 0.188 mole) in acetic anhydride (15 ml) was refluxed for 5 h. The solution was allowed to cool to room temperature to give pale yellow solid. The solid was filtered off under suction and the filter cake was washed with tetrahydrofuran. This was transferred into a conical flask, stirred with de-ionised water for 15 minutes and filtered off under suction. The solid was again washed with tetrahydrofuran and petroleum ether (40-60° C.). The product was dried under vacuum at 80° C. for 8 hours. Yield: 5.9 g. The product was sublimed to give a yellow-orange solid exhibiting intense yellow fluorescence. Its absorption and fluorescence spectra in thin film and in solution in THF are shown in FIGS. 1 and 2.

Yield: 2.8 g M.p 298° C. (DSC, onset), 303° C. (DSC, peak); $T_g$ 111° C.

| Element | C | H | N | S |
|---|---|---|---|---|
| % Theory | 72.70 | 4.07 | 7.06 | 16.17 |
| % Found | 72.85 | 4.12 | 7.10 | 16.17 |

Device Structure

A pre-etched ITO coated glass piece (10×10 cm$^2$) was used. The device was fabricated by sequentially forming layers on the ITO, by vacuum evaporation using a Solciet Machine, ULVAC Ltd. Chigacki, Japan. The active area of each pixel was 3 mm by 3 mm. The coated electrodes were encapsulated in an inert atmosphere (nitrogen) with UV-curable adhesive using a glass back plate. Electroluminescence studies were performed with the ITO electrode was always connected to the positive terminal. The current vs. voltage studies were carried out on a computer controlled Keithly 2400 source meter.

EXAMPLE 1

Devices with red and blue green emission were formed by the method described above consisting of an anode layer, buffer layer, hole transport layer, electroluminescent layer (doped material), electron transport layer, electron injection layer and cathode layer, film thicknesses being in nm:

Red

ITO/ZnTp TP (20)/α-NBP(50)/Alq$_3$:DCJTi (60:0.6)/ETL (20)/LiF(0.3)/Al wherein the ETL is Zrq$_4$ or 2,9-Bis(2-thiophen-2-yl-vinyl)-[1,10]phenanthroline.

Blue

ITO/ZnTp TP (20)/α-NBP(50)/Compound H:perylene (25:0.1)/ETL (20)/LiF(0.3)/Al wherein the ETL is Zrq$_4$ or 2,9-Bis(2-thiophen-2-yl-vinyl)-[1,10]phenanthroline.

Green

As indicated in FIGS. 9-12

Results are shown in FIGS. 3-12.

EXAMPLE 2

Preparation of 2,9-Bis (2-aryl vinyl)-[1,10]phenanthrolines

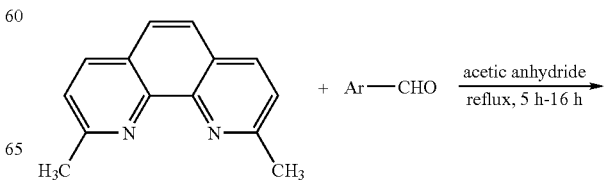

-continued

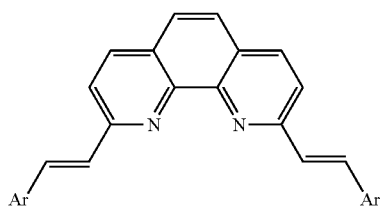

A mixture of 2,9-dimethyl-1,10-phenanthroline (neocuproine hydrate) (5.0 g; 0.024 mole) and 2-Aryl carboxaldehyde (0.053 mole) in acetic anhydride (20 ml) was refluxed for 5-16 h. The cooled reaction mixture was poured into methanol/water to give a solid. The solid was filtered off taken-up in dichloromethane by dissolving the solid and extracted with water in a separating funnel. The organic phase was washed with de-ionized water, dried over anhydrous magnesium sulphate and evaporated to give a solid, yield 55%-75%. The product was sublimed to give an analytically pure solid exhibiting intense fluorescence.

The compounds listed below were made by the above procedure:

| Name | Structure | EA (%) Theory Fouund | M. Pt. DSC Peak (°C.) | Tg (°C.) | UV-Vis. $\lambda_{max}$ (nm) Solution | FL. $\lambda_{max}$ (nm) Solution |
|---|---|---|---|---|---|---|
| Compound B | 2,9-Bis(4,4'-trifluoromethyl styrenyl) phenenthroline | C = 69.23  C = 69.54<br>H = 3.49    H = 3.39<br>N = 5.38    N = 5.40 | 279 | No Tg | 355<br>307<br>241 | 397 |
| Compound C | 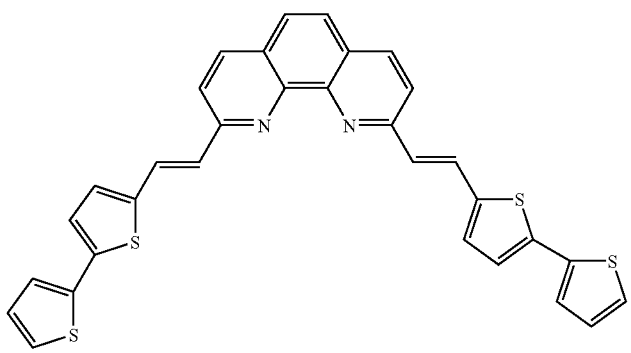 [SMILES: C(=C\c1ccc(-c2cccs2)s1)/c1ccc2ccc3ccc(/C=C/c4ccc(-c5cccs5)s4)nc3c2n1] | C = 68.54  C = 68.38<br>H = 3.59    H = 3.58<br>N = 5.00    N = 4.91 | No peak | No Tg | To be determined | To be determined |
| Compound D | 2,9-Bis(4,4'-cyanostyrenyl) phenanthroline | C = 82.93  C = 82.67<br>H = 4.18    H = 4.07<br>N = 12.82  N = 12.82 | 289 | No Tg | To be determined | To be determined |

-continued

| Name | Structure | EA (%) Theory Found | M. Pt. DSC Peak (°C.) | Tg (°C.) | UV-Vis. $\lambda_{max}$ (nm) Solution | FL. $\lambda_{max}$ (nm) Solution |
|---|---|---|---|---|---|---|
| Compound E | 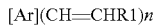 2,9-Bis(2,2'-Vinyl-5,5'-phenyl thiophenyl) phenanthroline | C = 78.80 C = 78.36<br>H = 4.41 H = 4.97<br>N = 5.10 N = 5.64 | 208 | No Tg | To be determined | To be determined |

The invention claimed is:

1. A compound of formula

[Ar](CH=CHR1)n wherein
n is an integer from 1 to 4;
Ar is a phenanthroline scaffold and
R1 is a 5-membered heteroaryl group represented by a thiophene ring optionally substituted with methyl, methoxy, aryl, or heteroaryl, or is phenyl or naphthyl substituted with methyl, methoxy, trifluoromethyl, or is biphenyl, or is substituted biphenyl.

2. An optical light emitting diode device comprising a first electrode, a layer comprising the compound of claim 1, and a second electrode.

3. The optical light emitting diode device of claim 2, comprising an electroluminescent layer and an electron transport layer, wherein said electron transport layer comprises a compound of formula

[Ar](CH=CHR1)n wherein
n is an integer from 1 to 4;
Ar is a phenanthroline scaffold; and
R1 is a 5-membered heteroaryl group represented by a thiophene ring optionally substituted with methyl, methoxy, aryl, or heteroaryl, or is phenyl or naphthyl substituted with methyl, methoxy, trifluoromethyl, or is biphenyl, or is substituted biphenyl.

4. The optical light emitting diode device of claim 3, wherein the electroluminescent layer comprises a doped compound of formula

[Ar](CH=CHR1)n wherein
n is an integer from 1 to 4;
Ar is a phenanthroline scaffold; and
R1 is a 5-membered heteroaryl group represented by a thiophene ring optionally substituted with methyl, methoxy, aryl, or heteroaryl, or is phenyl or naphthyl substituted with methyl, methoxy, trifluoromethyl, or is biphenyl, or is substituted biphenyl.

5. The optical light emitting diode device of claim 3, wherein said electroluminescent layer comprises a metal complex.

6. The optical light emitting diode device of claim 5, wherein said electroluminescent layer comprises zirconium or hafnium quinolate as host material doped with a dopant.

7. The optical light emitting diode device of claim 5, wherein said electroluminescent layer comprises aluminium quinolate as the host material doped with a dopant.

8. The optical light emitting diode device of claim 3, wherein said electroluminescent layer comprises an aromatic tertiary amine as host material doped with a dopant.

9. The optical light emitting diode device of claim 3, wherein said electroluminescent layer comprises a light emitting material which is a metal or metalloid complex.

10. The optical light emitting diode device of claim 9, wherein said electroluminescent layer comprises as luminescent material a metal quinolate, an iridium, ruthenium, osmium, rhodium, iridium, palladium, or platinum complex, a boron complex, or a rare earth complex.

11. The optical light emitting diode device of claim 9, wherein said electroluminescent layer comprises as electroluminescent material lithium quinolate or aluminium quinolate.

12. The optical light emitting diode device of claim 3, wherein said electroluminescent layer comprises a light-emitting conjugated polymer or copolymer or a dendrimer.

13. The optical light emitting diode device of claim 2, comprising a hole injection layer comprising ZnTpTP.

14. The optical light emitting diode device of claim 2, comprising a hole transport layer comprising α-NBP.

15. An electro-optical or opto-electronic device comprising a layer comprising the compound of claim 1.

16. The electro-optical or opto-electronic device of claim 15, wherein said electro-optical or opto-electronic device is a flat panel display.

17. The electro-optical or opto-electronic device of claim 15, wherein said electro-optical or opto-electronic device is an imaging member for creation of an electrostatic latent image.

18. A compound of formula

[Ar](CH=CHR1)n wherein
n is an integer from 2 to 4;
Ar is a phenanthroline scaffold and
R1 is a 5-membered heteroaryl group optionally substituted with methyl, methoxy, aryl, or heteroaryl, or is phenyl or naphthyl substituted with methyl, methoxy, trifluoromethyl, or is biphenyl, or is substituted biphenyl.

19. An optical light emitting diode device comprising a first electrode, a layer comprising the compound of claim 18, and a second electrode.

20. The optical light emitting diode device of claim 19, comprising an electroluminescent layer and an electron transport layer, wherein said electron transport layer comprises a compound of formula

[Ar](CH=CHR1)n wherein
n is an integer from 2 to 4;
Ar is a phenanthroline scaffold optionally substituted with one or more alkyl or alkoxy groups; and
R1 is a 5-membered heteroaryl group optionally substituted with methyl, methoxy, aryl, or heteroaryl, or is phenyl or naphthyl substituted with methyl, methoxy, trifluoromethyl, or is biphenyl, or is substituted biphenyl.

21. The optical light emitting diode device of claim 19, wherein the electroluminescent layer comprises a doped compound of formula

[Ar](CH=CHR1)n wherein
n is an integer from 2 to 4;
Ar is a phenanthroline scaffold optionally substituted with one or more alkyl or alkoxy groups; and
R1 is a 5-membered heteroaryl group optionally substituted with methyl, methoxy, aryl, or heteroaryl, or is phenyl or naphthyl substituted with methyl, methoxy, trifluoromethyl, or is biphenyl, or is substituted biphenyl.

22. The optical light emitting diode device of claim 20, wherein said electroluminescent layer comprises a metal complex.

23. The optical light emitting diode device of claim 22, wherein said electroluminescent layer comprises zirconium or hafnium quinolate as host material doped with a dopant.

24. The optical light emitting diode device of claim 22, wherein said electroluminescent
layer comprises aluminum quinolate as the host material doped with a dopant.

25. The optical light emitting diode device of claim 19, wherein said electroluminescent layer comprises an aromatic tertiary amine as host material doped with a dopant.

26. The optical light emitting diode device of claim 19, wherein said electroluminescent layer comprises a light emitting material which is a metal or metalloid complex.

27. The optical light emitting diode device of claim 26, wherein said electroluminescent layer comprises as luminescent material a metal quinolate, an iridium, ruthenium, osmium, rhodium, iridium, palladium, or platinum complex, a boron complex, or a rare earth complex.

28. The optical light emitting diode device of claim 26, wherein said electroluminescent layer comprises as electroluminescent material lithium quinolate or aluminum quinolate.

29. The optical light emitting diode device of claim 20, wherein said electroluminescent layer comprises a light-emitting conjugated polymer or copolymer or a dendrimer.

30. The optical light emitting diode device of claim 19, comprising a hole injection layer comprising ZnTpTP.

31. The optical light emitting diode device of claim 19, comprising a hole transport layer comprising a-NBP.

32. An electro-optical or opto-electronic device comprising a layer comprising the compound of claim 18.

33. The electro-optical or opto-electronic device of claim 32, wherein said electro-optical or opto-electronic device is a flat panel display.

34. The electro-optical or opto-electronic device of claim 32, wherein said electro-optical or opto-electronic device is an imaging member for creation of an electrostatic latent image.

* * * * *